(12) United States Patent
Boulet et al.

(10) Patent No.: US 11,033,592 B2
(45) Date of Patent: Jun. 15, 2021

(54) COMPOSITION FOR THE PREVENTION AND/OR TREATMENT OF CARDIOVASCULAR DISEASES

(71) Applicant: Groupe Santé Devonian Inc., Montmagny (CA)

(72) Inventors: André P. Boulet, Blainville (CA); Theophilus J. Gana, Leesburg, VA (US); Nathalie Boucher, Trois-Riviéres (CA)

(73) Assignee: GROUPE SANTÉ DEVONIAN INC., Montmagny (CA)

( * ) Notice: Subject to any disclaimer, the term of this patent is extended or adjusted under 35 U.S.C. 154(b) by 0 days.

(21) Appl. No.: 16/347,613

(22) PCT Filed: Nov. 3, 2017

(86) PCT No.: PCT/CA2017/051306
§ 371 (c)(1),
(2) Date: May 6, 2019

(87) PCT Pub. No.: WO2018/081903
PCT Pub. Date: May 11, 2018

(65) Prior Publication Data
US 2019/0314433 A1    Oct. 17, 2019

Related U.S. Application Data

(60) Provisional application No. 62/417,415, filed on Nov. 4, 2016.

(51) Int. Cl.
| | |
|---|---|
| *A61K 36/00* | (2006.01) |
| *A61K 36/21* | (2006.01) |
| *A61P 9/00* | (2006.01) |
| *A61K 9/00* | (2006.01) |
| *A61K 31/015* | (2006.01) |
| *A61K 31/065* | (2006.01) |
| *A61K 31/409* | (2006.01) |

(52) U.S. Cl.
CPC ............ *A61K 36/21* (2013.01); *A61K 9/0053* (2013.01); *A61K 31/015* (2013.01); *A61K 31/065* (2013.01); *A61K 31/409* (2013.01); *A61P 9/00* (2018.01)

(58) Field of Classification Search
None
See application file for complete search history.

(56) References Cited

U.S. PATENT DOCUMENTS

2011/0182930 A1*   7/2011   Erlanson-Albertsson ..................
A61P 5/48
424/195.17

FOREIGN PATENT DOCUMENTS

| WO | 01/49305 A2 | 7/2001 |
| WO | 03/004042 A1 | 1/2003 |
| WO | 2005/027944 A1 | 3/2005 |

OTHER PUBLICATIONS

Matthijs, Purification of membrane-bound ferredoxin: NADP(+) oxidoreductase and of plastocyanin from a detergent extract of washed thylakoids. Photosynthesis research, (Jan. 1987) vol. 12, No. 3, pp. 273-281 (Year: 1987).*
Atherosclerosis from Wikipedia, accessed on Nov. 6, 2020, pp. 1-22 (Year: 2020).*
PCT International Search Report and Written Opinion for PCT Application No. PCT/CA2017/051306 dated Jan. 9, 2018 (10 pages).
Shrivastava et al., "Serial Measurement of Lipid Profile and Inflammatory Markers in Patients with Acute Myocardial Infarction," EXCLI Journal, 2015, 14:517-526.
European Search Report for EP Application No. 17867471.9 dated May 29, 2020 (7 pages).
Richardson Gmp Limited: "Preliminary Prospectus for Orletto Capital Inc.", Group Devonian, Aug. 12, 2016, pp. 1-134 (http://groupedevonian.com/en/wp-content/uploads/2016/11 / PRELIMINARYPROSPCECTUS-1.pdf).
Kohnke et al., "Thylakoids Suppress Appetite by Increasing Cholecystokinin Resulting in Lower Food Intake and Body Weight in High-fat Fed Mice," Phytotherapy Res., 2009, 23(12):1778-1783.

* cited by examiner

*Primary Examiner* — Qiuwen Mi
(74) *Attorney, Agent, or Firm* — Eversheds Sutherland (US) LLP

(57) ABSTRACT

There is provided the use of a functional thylakoid extract, particularly in admixture with a physiologically acceptable carrier, in pharmaceutical application, in the treatment of cardiovascular diseases, and method for the treatment thereof. The cardiovascular diseases (CVD) may comprise several diseases associated with inflammation of the heart or arteries and include coronary artery diseases (CAD) such as angina and myocardial infarction (commonly known as a heart attack), atherosclerosis, stroke, hypertensive heart disease, rheumatic heart disease, cardiomyopathy, heart arrhythmia, congenital heart disease, valvular heart disease, carditis, aortic aneurysms, peripheral artery disease, and venous thrombosis.

11 Claims, 12 Drawing Sheets

COMPOSITION FOR THE PREVENTION AND/OR TREATMENT OF CARDIOVASCULAR DISEASES

RELATED APPLICATIONS

This application claims the priority benefit of PCT/CA2017/051306 filed on Nov. 3, 2017 which claims priority from U.S. provisional application No. 62/417,415 that was filed on Nov. 4, 2016, the entire contents of which are incorporated by reference in their entirety.

FIELD

This invention relates to a composition comprising functional thylakoids, particularly in specific formulations that ensure the integrity, stability and functionality of the thylakoids (i.e. functional thylakoid extract), and methods of use to prevent and/or treat cardiovascular disease such as stroke or atherosclerosis.

BACKGROUND

Inflammation is a process well known for its implication in acute and chronic diseases and disorders in the biomedical field. Although inflammation is a natural process associated with cell and tissue defense and regeneration, disorganized inflammation can contribute to (or is implicated in) many processes that are harmful to cells and tissues.

Inflammation is the body's reaction to infectious agents, antigen challenge or physical, chemical or traumatic injury. The main purpose of inflammation is to bring fluids, proteins, and cells from the blood into the damaged tissues. The main features of the inflammatory response are (i) vasodilation (widening of the blood vessels to increase blood flow); (ii) increased vascular permeability that allows diffusible components to enter the tissues; (iii) cellular infiltration by chemotaxis, or directed movement of inflammatory cells through the walls of blood vessels into the site of injury; (iv) changes in biosynthetic, metabolic, and catabolic profiles of the affected tissues; and (v) activation of cells of the immune system as well as enzymatic systems of the blood plasma.

In general, the inflammatory response is quite efficient in managing and repairing damages induced by injury or infectious agents. The degree to which these phenomena occur is normally proportional to the severity of the injury or the extent of the challenge. However, inflammation can become harmful to tissues when it develops in a disorganized, disproportionate or undesired manner and can lead to chronic disease or disorder.

WO 01/49305 discloses anti-oxidative compositions and method for their extraction. WO 03/04042 discloses their use in combination with other anti-inflammatory compounds. WO 2005/027944 discloses an oral formulation for the administration as anti-inflammatory compounds.

Chronic inflammatory reaction may be seen as a long-lasting inflammation, where the inflammatory agent is continually present. However, chronic inflammation is often seen in cases where the inflammatory agent is not present, as is the case for cardiovascular diseases. In this case, one or more inflammatory components contribute to the etiology and perpetuation of inflammation.

It has been shown that interventions at the level of certain markers may prevent diseases provoked thereof. A case in point, inhibition of LTB4 has been shown to prevent endothelial injury and reverses pulmonary hypertension (Tian et al., 2013). As well, the role of inflammation in the propagation of atherosclerosis and susceptibility to cardiovascular events is well established. Inflammation is central to the initiation and progression of atherothrombosis and triggering cardiovascular disease events (Yousuf et al., 2013).

Of the wide array of inflammatory biomarkers that have been studied, high-sensitivity C-reactive protein (hsCRP) has received the most attention for its use in screening and risk reclassification. Multiple studies suggest the association of low-level chronic inflammation during atherogenesis and demonstrate that CRP is a risk predictor of cardiovascular disease. (Albert, 2011, Yousuf et al., 2013). High sensitivity C-reactive protein is associated with the buildup of cholesterol and other fatty material in the coronary arteries. CRP is an acute phase reactant produced by the liver, strongly regulated by IL-6 concentrations (Albert, 2011).

In 2003, the Centers for Disease Control and Prevention and the American Heart Association (AHA) recommended that CRP could be used as a global assessment of cardiovascular risk (Pearson et al., 2003). Other national and medical agencies have followed and recommended this CRP assessment in patient at intermediate risk for a cardiovascular event: in 2009 for the Canadian Cardiovascular Society (Genest et al., 2009) and the National Academy of Clinical Biochemistry Medicine Practice Guidelines (Meyers et al, 2009) and in 2010 for the American College of Cardiology Foundation-AHA (Greenland et al., 2010).

As well, superoxides play important roles in the pathogenesis of many cardiovascular diseases, including hypertension and atherosclerosis (Fukai and Fukai, 2011). SODs also play a critical role in endothelial and mitochondrial function by inhibiting oxidative pathway of bioavailable NO (Fukai and Fukai, 2011). The expression of SOD is decreased in myocardial infarction (MI)-induced failing heart (van Deel et al., 2008).

Furthermore, NO is synthesized by 4 nitric oxide synthases (NOS) through a series of redox reactions. These are endothelial nitric oxide synthase (eNOS), inducible nitric oxide synthase (iNOS), neuronal nitric oxide synthase (nNOS) and mitochondrial nitric oxide synthase (Li et al., 2015). eNOS and nNOS are constitutively expressed in cardiomyocytes (Arcaro et al., 2015). While inducible iNOS is absent in the normal myocardium, this enzyme is expressed by proinflammatory mediators (Arcaro et al., 2015). It was demonstrated in a case study with patients having coronary artery disease associated to hypertension, that harmful NO was produced due to an increase to iNOS activity (Besedina, 2016). iNOS is also elevated in the myocardium of patients with heart failure (McNeil and Channon, 2012). iNOS has been reported to be deleterious in atherosclerotic plaque progression and ischemia-reperfusion injury (McNeil and Channon, 2012). NO is a key mediator of immunity by regulating immune responses. In association with reactive oxygen species (ROS), it triggers the eradication of pathogens. Abnormalities in NO generation or activity have been proposed as a major mechanism of coronary heart disease (Besedina, 2016). It has been argued that pulmonary arterial hypertension is probably a NO/ONOO-cycle disease, suggesting that other types of cardiovascular diseases may also be candidates for being caused by iNOS elevation (Pall, 2013).

Therefore, there is a need to develop new compositions and formulations for the prevention and/or treatment chronic inflammation, particularly cardiovascular diseases that are mainly caused by chronic inflammation.

SUMMARY

Therefore, there is provided a composition (named herein Composition A), comprising a functional thylakoid extract, or a pharmaceutical formulation thereof, and its use for decreasing a level of blood CRP or hsCRP in mammal, wherein the level of CRP or hsCRP prior to administration of the composition is indicative of chronic inflammation.

Thus, there is also provided a composition (named herein Composition A), comprising a functional thylakoid extract, or a pharmaceutical formulation thereof, and its use in the prevention and/or treatment of cardiovascular diseases.

In a first aspect, there is provided a composition to treat cardiovascular diseases (CVD) in a subject, the composition comprising an effective amount of a functional thylakoid extract, particularly in admixture with a physiologically acceptable carrier.

In a second aspect, there is provided use of a functional thylakoid extract in the manufacture of a medication for preventing or treating cardiovascular diseases (CVD) in a subject.

In a further aspect, there is provided use of a functional thylakoid extract for preventing or treating cardiovascular diseases (CVD) in a subject.

In an alternative aspect, there is provided a formulation for the oral prevention or treatment of cardiovascular diseases, comprising a functional thylakoid extract, in admixture with an orally-acceptable excipient, and optionally a preservative.

In a further aspect, there is also provided a method for preventing or treating cardiovascular diseases (CVD) in a subject in need thereof, comprising administering to said subject an effective amount of a functional thylakoid extract, optionally in admixture with a physiologically acceptable carrier.

In a further aspect, there is also provided a composition for decreasing a baseline level of blood CRP or blood hsCRP in a mammal by at least about 25% after 14 days, comprising a thylakoid extract comprising purified functional photosynthetic pigments in their thylakoid membrane environment, wherein said baseline level of CRP or hsCRP prior to administration of the composition is indicative of chronic inflammation.

In a further aspect, there is also provided a use of a thylakoid extract comprising purified functional photosynthetic pigments in their thylakoid membrane environment in the manufacture of a medication for decreasing blood CRP or blood hsCRP in a subject, wherein said decrease is at least 25% of baseline and said baseline level of CRP or hsCRP prior to administration of the composition is indicative of chronic inflammation.

In a further aspect, there is provided a method for decreasing a baseline level of blood CRP or blood hsCRP in a subject in need thereof, comprising administering to said subject an effective amount of a thylakoid extract comprising purified functional photosynthetic pigments in their thylakoid membrane environment, wherein said baseline level of CRP or hsCRP prior to administration of the composition is indicative of chronic inflammation, and said effective amount comprises decreased said baseline level by least about 25% after 14 days.

Other objects, advantages and features of the present invention will become more apparent upon reading of the following non-restrictive description of preferred embodiments thereof, given by way of example only with reference to the accompanying drawings.

The contents of the documents cited in the present disclosure are incorporated by reference thereto.

DETAILED DESCRIPTION

ABBREVIATIONS AND DEFINITIONS

Abbreviations

Figure 1:
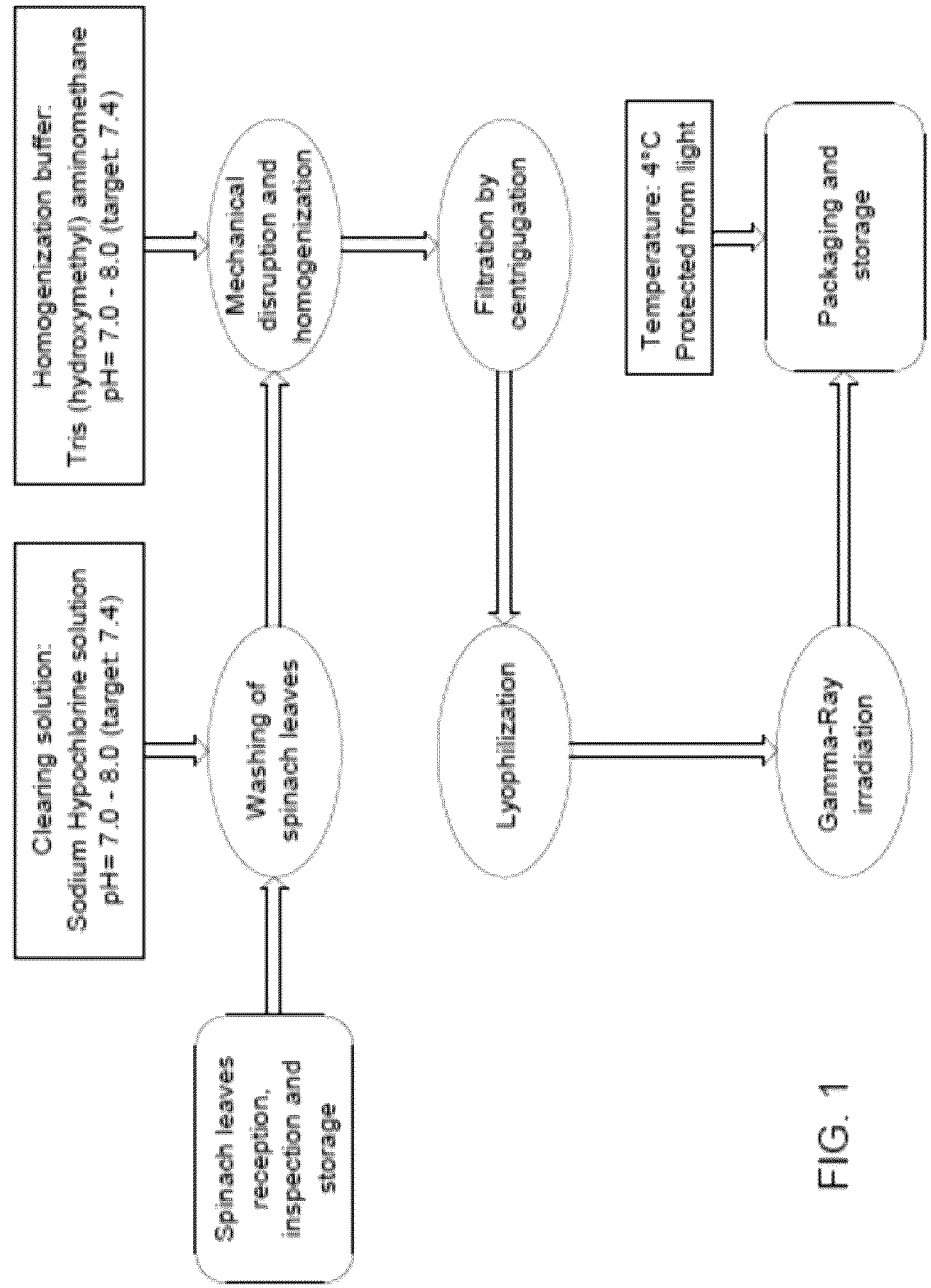
FIG. 1. Flow-diagram of composition A manufacturing process.

AE: adverse events; SAE: serious adverse events; Cp A: composition A of the present invention; CRP: serum C-reactive protein; hs CRP: serum high sensitivity CRP; ESR: erythrocyte sedimentation rate; FC; fecal Calprotein; FL: fecal Lactoferrin; LTB: serum Leukotriene B; M30: change from baseline to day 14 in M30 Apoptosome level in biopsy tissue.

Definitions

The term "about" as used herein refers to a margin of + or −10% of the number indicated. For the sake of precision, the term about when used in conjunction with, for example: 90% means 90%+/−9% i.e. from 81% to 99%. More precisely, the term about refer to + or −5% of the number indicated, where for example: 90% means 90%+/−4.5% i.e. from 86.5% to 94.5%.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

The terms: "thylakoid", "thylakoid extract", "functional thylakoid extract" or "functional thylakoid" or "active thylakoids/extract" as used herein, means purified functional photosynthetic pigments in a thylakoid membrane environment (i.e. in an integral native state such that they can still be active or activated), particularly their original thylakoid environment. More particularly, these terms refer to functional thylakoid membranes as extracted by the process herein described and/or by the procedure disclosed in Bissonnette et al. (2004) or WO01/49305.

Particularly, in connection with an aspect of the present thylakoid extract, the functional quality of the molecular complex can be measured by fluorescence based on its capacity to react to light and dissipate its energy ($F_v/F_m$ ratio), as is well known in the art and/or described in Maxwell (2000).

Detailed Description of Particular Embodiments

Unexpectedly, the present Applicants have discovered that high levels of hsCRP are decreased upon administration of an active thylakoid extract in patients suffering from ulcerative colitis.

High-sensitivity C-reactive protein (hsCRP) is associated with low-level chronic inflammation during atherogenesis, buildup of cholesterol and other fatty material in the coronary arteries. Hence, CRP constitutes a risk predictor of cardiovascular disease. In 2003, CRP was recommended to be used as a global assessment of cardiovascular risk and this CRP is recommended in the assessment in patient at intermediate risk for a cardiovascular event.

Therefore, in accordance with a main aspect, there is provided a composition (named herein Composition A or (Cp A), comprising a functional thylakoid extract, or a pharmaceutical formulation thereof, and its use for decreasing a level of blood CRP or hsCRP in mammal, wherein the level of CRP or hsCRP prior to administration of the composition is indicative of chronic inflammation.

Hence, in accordance with the present invention, there is provided a use of composition comprising a functional thylakoid extract (or a pharmaceutical formulation thereof) in prevention and/or treatment of cardiovascular diseases.

Composition

In accordance with a particular aspect, the invention describes a composition to treat cardiovascular diseases (CVD) in a subject, comprising an effective amount of an active thylakoid extract, particularly in admixture with a physiologically acceptable carrier. Particularly, the thylakoid extract is a spinach thylakoid extract, and more particularly extracted from spinach leaves.

Particularly the composition comprises purified functional photosynthetic pigments in a thylakoid membrane environment. Still particularly, the extract is quiescent and can be activated photosynthetically. More particularly, the extract is stabilized in its fundamental state (i.e. stable) by being devoid of any electron donor (such as water).

Most particularly, the composition is called Composition A and is defined as a raw organic spinach, active thylakoid extract, wherein the ratio chlorophyll a to total pigment is at least 0.4, particularly at least 0.5, more particularly at least 0.6.

In particular, the pigment comprised in the thylakoid extract is selected from the group consisting of: chlorophyll a, chlorophyll b, and carotenoids. More particularly, the pigment comprised in the thylakoid extract is selected from the group consisting of: chlorophyll a, chlorophyll b, lutein, and optionally, β-carotene and/or pheophytin. Still, most particularly, the pigment comprised in the thylakoid extract consists essentially of: chlorophyll a (more than 40%), followed by chlorophyll b (about 10-15%), lutein (about 10% or less), β-carotene (about 3%) and pheophytin (less than 1%).

Stabilized Extract

Particularly, the extract is stabilized in its fundamental state (i.e. stable) by being devoid of any electron donor (such as water). More particularly, the extract is stabilized by containing no more than 10% of water (or other electron donor), particularly less than 10% water.

The composition may be in powder form, such as a lyophilized dried composition, or may be admixed with physiologically-acceptable solid or liquid excipients, such as: PEG or DMSO to form a stabilized solution of suspension, inasmuch as the composition remains free, or substantially free, of electron donors (such as water), to maintain activity of the functional pigments.

Particularly, the stabilized extract is in solid form, more as particularly, as a powder. Still, more particularly, the extract is in powder form with at least 25 mg pigments per gram of powder. More particularly, the raw powder may be compressed in tablets, encapsulated, or packaged into aliquot packets or pouches. Alternatively, the powder may be mixed with suppository excipients and molded to form suppositories.

Alternatively, the stabilized extract is in liquid form, such as solution or suspension, in a liquid excipient devoid of water or electron donor, such as for example, PEG or DMSO. Particularly, the stabilized solution or suspension may be diluted in a liquid shortly or immediately before administration. Most particularly, for oral administration, the liquid may be water, juice, syrup, etc. Alternatively, for rectal administration, the liquid may be an enema formulation.

Uses

In accordance with a particular aspect, there is provided use of a thylakoid extract comprising purified functional photosynthetic pigments in a thylakoid membrane environment in the making of a medication for treating or delaying onset of cardiovascular diseases (CVD) in a subject.

Alternatively, there is provided use of a thylakoid extract comprising purified functional photosynthetic pigments in a thylakoid membrane environment for treating or delaying onset of cardiovascular diseases (CVD) in a subject.

Particularly, the use of the composition A is provided in the context where the CVD is selected from: angina, stroke, myocardial/cerebral infraction, atherosclerosis, bypass surgery, ischemia, hypertensive heart disease, rheumatic heart disease, cardiomyopathy, heart arrhythmia, congenital heart disease, valvular heart disease, carditis, aortic aneurysms, peripheral artery disease, venous thrombosis, unstable angina, and arterial revascularization.

Method of Treatment

In accordance with a particular embodiment, there is provided a method for treating cardiovascular diseases (CVD) in a subject in need thereof, comprising administering to the subject an effective amount of a thylakoid extract comprising purified functional photosynthetic pigments in a thylakoid membrane environment, particularly in admixture with a physiologically acceptable carrier. Particularly, the method of treatment is provided in the context of treating: angina, stroke, myocardial/cerebral infraction, atherosclerosis, bypass surgery, ischemia, hypertensive heart disease, rheumatic heart disease, cardiomyopathy, heart arrhythmia, congenital heart disease, valvular heart disease, carditis, aortic aneurysms, peripheral artery disease, venous thrombosis, unstable angina, and arterial revascularization.

Therapeutic Indications

Particularly, the cardiovascular diseases (CVD) may comprise several diseases associated with inflammation of the cardiovascular system such as, by way of non-limiting examples, angina, stroke, myocardial/cerebral infraction, atherosclerosis, bypass surgery, ischemia, hypertensive heart disease, rheumatic heart disease, cardiomyopathy, heart arrhythmia, congenital heart disease, valvular heart disease, carditis, aortic aneurysms, peripheral artery disease, venous thrombosis, unstable angina, and arterial revascularization.

Particularly, the CVD is angina, stroke, myocardial infraction, ischemia, venous thrombosis and atherosclerosis Subjects In particular, the present use and method may be indicated for the treatment of mammalian subjects, particularly pets or human, more particularly cats, dogs, horses, or human, most particularly humans.

Formulation

In accordance with a particular aspect, there is provided the use or the method of treatment as defined herein, wherein the composition is formulated for oral administration.

Particularly, the oral formulation is in the form of a tablet, capsule, caplet, powder, pellet, syrup, etc.

More particularly, the composition is formulated for parenteral administration. Most particularly, the composition is formulated for intra-cardiac administration immediately after a heart attack (myocardial infarction) or up to 24 hours after a heart attack (myocardial infarction).

Dosage

As used herein, the terms "effective amount" means a dose sufficient to induce a reduction in CVD symptoms or a reduction in markers of inflammation associated with CVD, and may be dependent on the subject being treated, the history of disease and/or the severity of symptoms. In particular, the expression "effective amount" means a dose sufficient to reduce CRP or hsCRP by at least about 10%, about 15%, about 20%, about 25%, about 40%, about 50%, about 60% after 14 days compared to a baseline level indicative of chronic inflammation. Particularly, a CRP or hsCRP baseline level of 2 mg/L or greater is indicative of chronic inflammation.

In accordance with a particular embodiment, the extract comprises an effective amount of about 0.00005 to 500 mg per Kg of subject's body weight, more particularly from about 0.001 to 20 mg per Kg of subject's body weight, most particularly from about 0.05 to 15 mg per Kg of subject's body weight, and still most particularly, from 0.5 to 10 mg per Kg of subject's body weight.

In accordance with a particular embodiment, the extract is provided at a dosage between about 250 to about 1000 mg/day, more particularly about 250, about 375, about 500, about 750, about 1000 or about 1500 mg/day, most particularly, about 250, 500 or 1000 mg/day.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

EXAMPLES

Example 1

Preparation of Thylakoid Extract (Composition A)

Composition A originates from the mesophyll tissue of baby spinach (*Spinacia oleracea* L.) leaves, which is rich in chloroplasts. The inner membranes of the chloroplasts, organized in structures known as thylakoids, are extracted from baby spinach, concentrated and stabilized into a solid powder form. The major constituents of thylakoid membranes are pigments, proteins and lipids.

TABLE 1

| Physical appearance: | Dark green powder |
|---|---|
| Solubility in water: | Insoluble |
| Solubility in alkaline medium (pH 10.6) | 0.5 mg/mL |
| Solubility in acidic medium (pH 1.0) | 0.3 mg/mL |

Manufacturing Process

The manufacturing process for Composition A is presented schematically in the flow diagram of FIG. 1.

The processing steps are executed with minimum light exposure and under cool conditions to preserve a maximal activity of the photosynthetic pigments. The steps are carried out in the following order: inspection of spinach leaves and washing with a sodium hypochlorite solution; mechanical disruption and homogenization; filtration by centrifugation; lyophilisation; and gamma-ray irradiation.

Inspection of spinach leaves and washing with a sodium hypochlorite solution. After visual inspection is performed to verify dimensional and identity attributes (e.g. leaves are green without discoloured zones or yellowish pecks (chlorose)), spinach leaves are first washed at a fixed solution-to-leaves ratio (44 kg:5.4 kg) on a mass basis, with a sodium hypochlorite solution adjusted to a pH between 7.0 and 8.0 (target pH: 7.4) to reduce the microbial flora naturally found on the leaves of fresh produce.

Mechanical disruption and homogenization. After draining the excess sodium hypochlorite solution, leaves are transferred into a mechanical cutter/mixer along with a fixed volume of Tris (hydroxymethyl) aminomethane buffer solution at pH between 7.0 and 8.0 (target pH: 7.4) at a fixed solution-to-leaves ratio (5.4 kg:3.7 kg) on a mass basis. This step is used to cut and homogenize the leaves into a coarse suspension while freeing up fragments of the thylakoid membranes originating from chloroplasts.

Filtration by centrifugation. The suspension is then filtered in a basket centrifuge. The centrifugation is performed at a target speed of 3100 rpm (range: 2800-3200 rpm). This step allows the removal of fibres, debris and coarse material which are retained on a screen, yielding a by-product cake to be discarded. Composition A, the active ingredient, is found in the centrifugate and is collected and kept at a temperature below 10° C. for further processing.

Lyophilisation. The material is then distributed over shallow stainless-steel plates and allowed to freeze in darkness at a temperature ≤−30° C. for a period of at least 2 hours. The plates kept at a target temperature of 10° C. are then transferred into a lyophilizer and the product is lyophilized.

Gamma-ray irradiation. A terminal gamma-ray irradiation step is carried out. After irradiation, Composition A is transferred into jars fitted with a tight screw cap.

Pigment Composition and Other Characteristics

Spinach contains natural antioxidants (e.g. flavonoids) and photosynthetic pigments (chlorophylls and carotenoids). The inner membranes of the chloroplasts are organized in structures known as thylakoids. The major constituents of thylakoid membranes are pigments, proteins and lipids.

Figure 2:
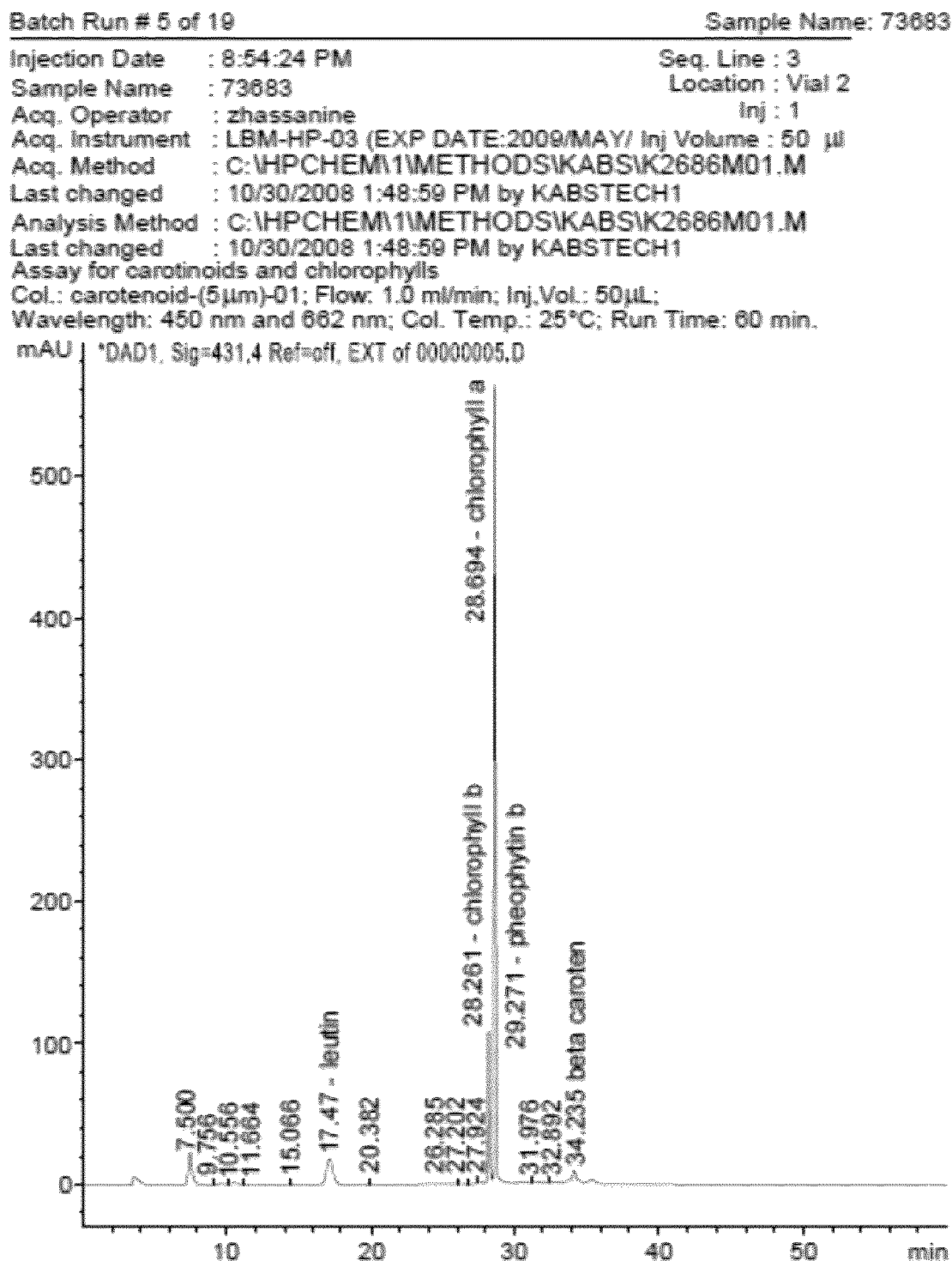
FIG. 2. HPLC chromatogram showing pigment profile of Composition A.
Figure 3A:
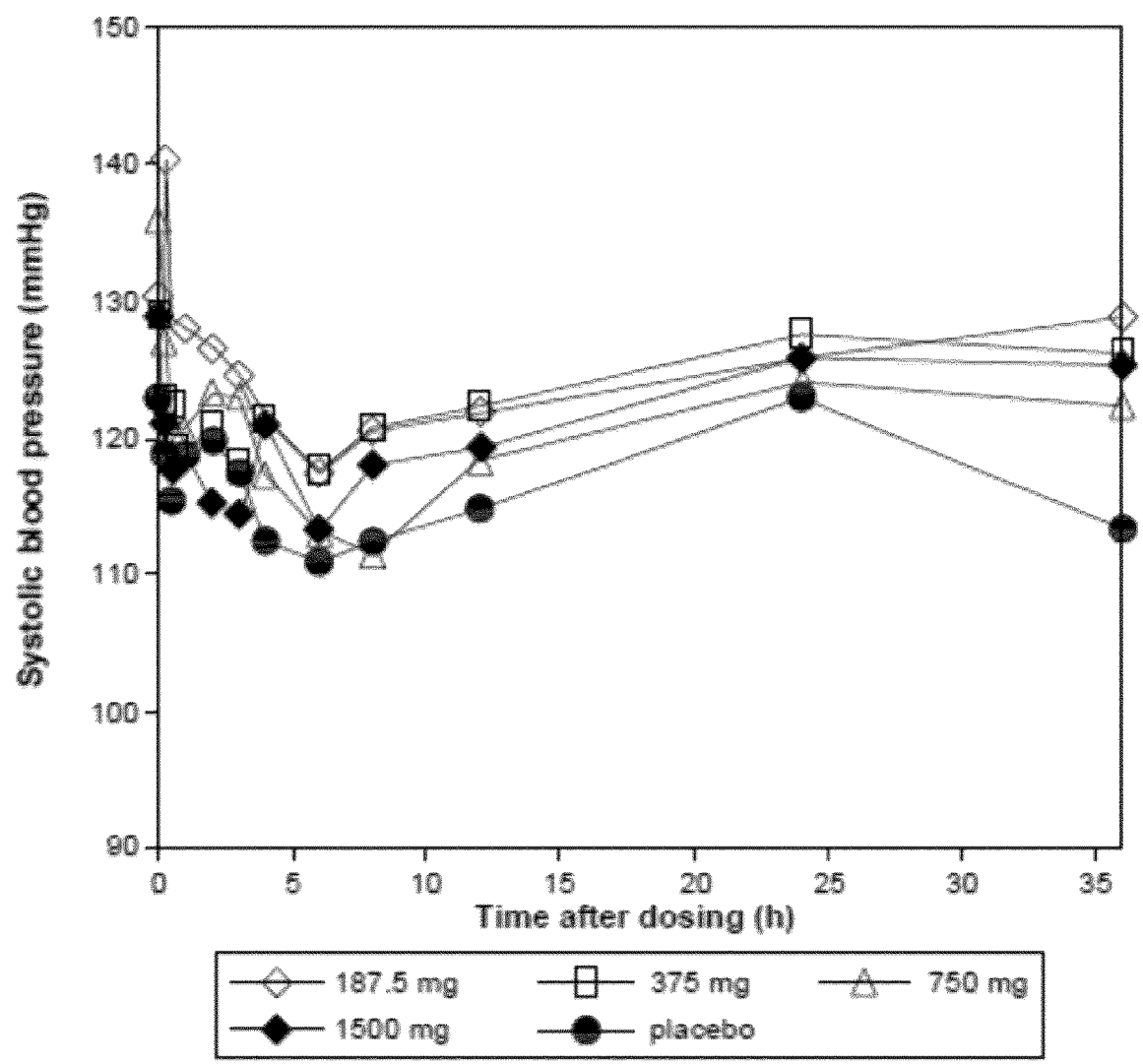
FIGS. 3A-3E. Mean time course of vital signs up to 36 hrs after dosing (Safety population). A) systolic blood pressure, B) diastolic blood pressure, C) pulse rate, D) respiratory rate, E) body temperature.
Figure 3B:
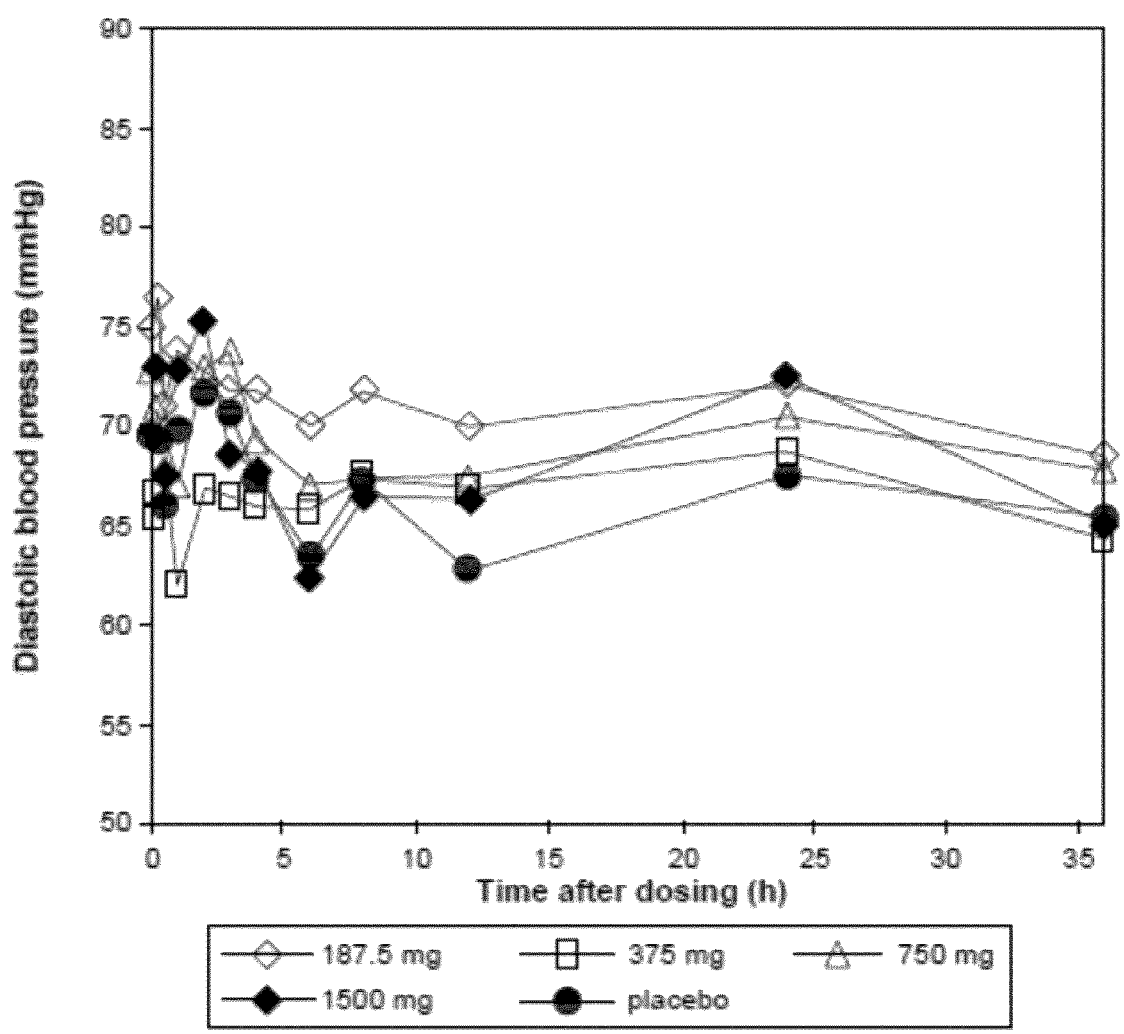
Figure 3C:
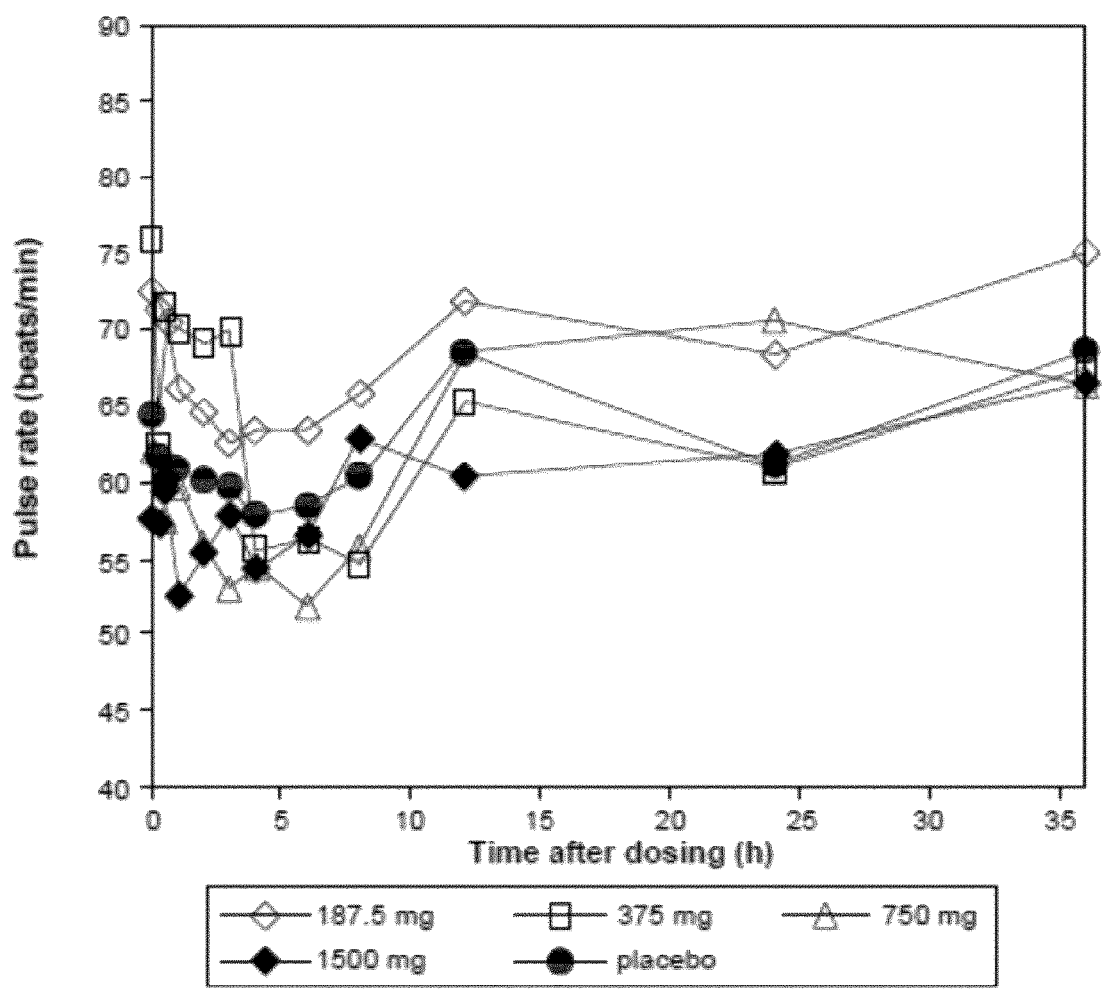
Figure 3D:
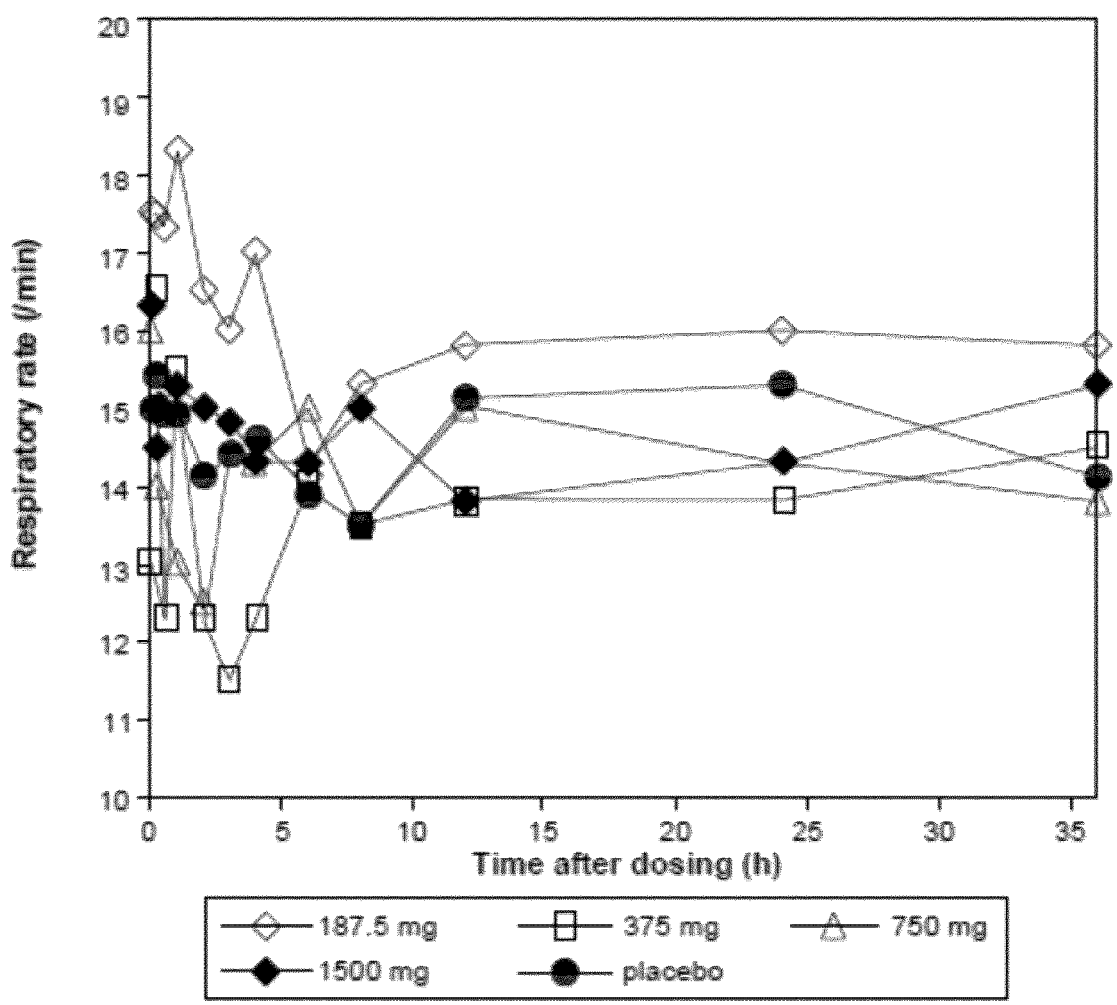
Figure 3E:
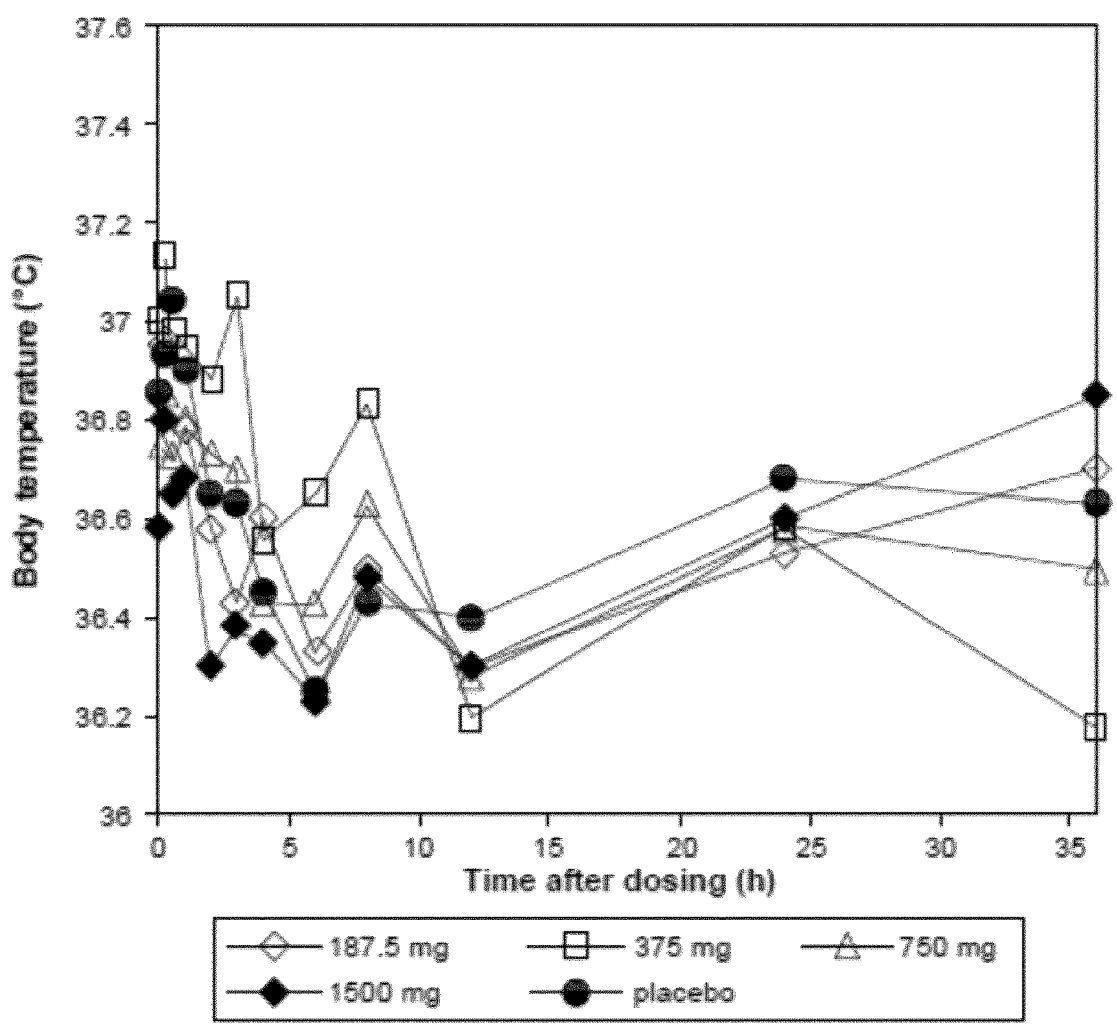

Composition A originates from the mesophyll tissue of spinach leaves which are rich in chloroplasts. To date, the following pigments have been identified in Composition A using HPLC analysis: lutein, chlorophyll b, chlorophyll a, pheophytin and β-carotene. A typical chromatogram showing the pigment profile of Composition A, in area %, is presented in FIG. 2. This analysis shows that the major constituent of Composition A is chlorophyll a (62.5%), followed by chlorophyll b (13.1%), lutein (9.4%), β-carotene (2.98%) and pheophytin (0.45%).

Preferably, raw baby spinaches were obtained from a grower certified as per the National Organic Standards of the United States Department of Agriculture (USDA) to minimize risks of presence of potential chemical residues from fertilizers or pesticides in Composition A.

Justification of Specification

Composition A is characterized by its pigment content expressed in milligram of pigment per gram of powdered extract. Based on process capabilities and allowing for seasonal variability in the herbal starting material, a specification of not less than 25 mg pigment/g extract was set. Based on stability data, a limit of 80% of the initial pigment content was set for shelf-life.

Pigment profile also allows identification of the various pigments present in Composition A and their ratios in area percent. Given the profile determined in batches, it was established that chlorophyll a, chlorophyll b, lutein and β-carotene should be present and that the average ratio of chlorophyll a to total peak area response should not be less than 0.40.

Since water is used as extraction solvent in the manufacturing process, a test to determine water content in Composition A has been included. A specification of not more than 10% w/w of water was set to control moisture.

The safety of the impurity levels present in Phase 1 clinical batch was qualified in a combined intrarectal single dose and 14-day repeat dose toxicity study in minipigs. As shown in Table 2, similar impurity levels were present in Phase 2 clinical batch. The maximum dose administered in the repeat dose toxicity study (200 mg/kg) was 14-fold higher than the maximum Phase 2 clinical trial dose (1000 mg or 14.3 mg/kg), which was administered once a day for 14 days. No toxicity findings of toxicological significance were observed in this study. A NOAEL for the significant events was justifiably defined as 200 mg/kg on the basis of microscopic minimal tubular degeneration in the kidneys, which was consistent with previously reported spontaneously occurring microscopic lesions in the Gottingen minipig.

TABLE 2

| SPECIFICATION FOR COMPOSITION A as a medicinal product | |
|---|---|
| Test | Acceptance criteria |
| PHYSICAL/CHEMICAL TESTING | |
| Description | Dark green powder |
| Total Pigment Content (mg/g) | Not less than 25 mg/g |
|  | End of shelf-life: NLT 80% of release content |
| Pigment Profile | |
| Lutein | Lutein, Chlorophyll a, chlorophyll b and β-carotene present |
| Chlorophyll b |  |
| Chlorophyll a | Average of ratio of Chlorophyll a against total peak area response not less than 0.40 |
| Pheophytin b |  |
| Beta carotene |  |
| Unknown |  |
| Tromethamine[a] Content (% w/w) | ≤5.0% w/w |
| Water Content (% w/w) | <10% w/w |
| Heavy Metals (µg/g) | ≤15% w/w |
| Residue on Ignition (%) | ≤5.0% |
| Cadmium (µg/g) | ≤15 µg/g |
| Chloride Content (%) | ≤1.5% |
| Pesticides Residues (mg/kg) | Below limit of detection in all cases |
| MICROBIOLOGICAL TESTING | |
| Aflatoxins | |
| $B_1$ | Not more than 2 ppb |
| $B_1, B_2, G_1, G_2$ | Not more than 4 ppb |
| Total Aerobic Microbial Count (CFU/g)[b] | $<1.0 \times 10^3$ |
| Yeasts and Moulds (CFU/g)[b] | $<1.0 \times 10^2$ |
| Total Anaerobic Sporulated Count (CFU/g)[c] | $<1.0 \times 10^1$ |

TABLE 2-continued

SPECIFICATION FOR COMPOSITION A as a medicinal product

| Test | Acceptance criteria |
|---|---|
| Pathogens | |
| *Escherichia coli* | Negative for all species |
| *Staphylococcus aureus* | |
| *Salmonella* sp. | |
| *Pseudomonas aeruginosa* | |

[a]Tris (hydroxymethyl) aminomethane
[b]Method based on USP <61> Microbial Limit Test
[c]Laboratory procedure in the Compendium of Analytical Methods of the Canadian Health Protection Branch of Health Canada Stability To date, two batches of Composition A medicinal product, packaged in a jar with a tight screw cap, have been placed on stability under the following conditions: 5° C.±3° C. (current recommended storage condition). The data available to date indicates that Composition A is stable after storage for at least 18 months under refrigerated conditions.

Example 2

Investigational Medicinal Product

Description and Composition of the Medicinal Product

The investigational medicinal product is a rectal enema which was reconstituted by patients prior to administration. The rectal enema was prepared by reconstituting Composition A drug substance or matching placebo powder with the reconstitution solution.

In order to do so, each patient received the following materials for each dose to be administered:
One bottle containing 60 g of reconstitution solution; and
One bottle containing either Composition A substance or matching placebo powder.

Three (3) doses of Composition A were administered in this study:
250 mg of Composition A in 60 g of reconstitution solution;
500 mg of Composition A in 60 g of reconstitution solution; or
1000 mg of Composition A in 60 g of reconstitution solution.

The placebo rectal enema was composed of 500 mg of matching placebo powder reconstituted in 60 g of reconstitution solution. The composition of the reconstitution solution is presented in Table 3.

TABLE 3

| Ingredient | Quantity per unit (mg/60 g) | Quantity per unit (%) | Function |
|---|---|---|---|
| Propylene Glycol USP | 3,000.00 | 5.000 | Suspending agent |
| Sodium Chloride USP | 450.00 | 0.750 | Osmolarity adjustment |
| Xanthan Gum, NF | 366.00 | 0.610 | Viscosity agent |
| Carbopol ® 980, NF | 72.00 | 0.120 | Viscosity agent |
| Methylparaben NF | 9.84 | 0.016 | Preservative |
| Propylparaben NF | 1.83 | 0.003 | Preservative |
| Ethylparaben NF | 1.83 | 0.003 | Preservative |
| Butylparaben NF | 1.83 | 0.003 | Preservative |
| Hydrochloric Acid NF | — | — | pH adjustment |
| Sodium Hydroxide NF | — | — | pH adjustment |
| USP Purified Water | 56,096.67 | 93.495 | Suspending solvent |

The composition of the matching placebo powder is presented in Table 4.

TABLE 4

| Ingredient | Quantity per unit (mg/60 g) | Quantity per unit (%) | Function |
|---|---|---|---|
| XH2664 US Green 3 Shade* | 1.0 | 0.1 | Colorant |
| FD&C Yellow No 6 (E110) spray-dried | 3.1 | 0.3 | Colorant |
| Sucrose, NF | 829.9 | 83.0 | Bulking ingredient and cryoprotectant |
| Pregelatinized Corn Starch, NF | 166.0 | 16.6 | Bulking ingredient and moisture control |
| Purified Water, USP | Removed during lyophilization | | Lyophilization solvent |

*Contains FD & C Blue No 1 (E133) and FD & C Yellow No 5 (E102). The Certificate of Compliance with EC Directive 95/45/EC on Food Colours and the FAO/WHO specification can be found in Annex 4

The formula of the reconstitution solution was typical of retention rectal enemas and was composed of ingredients of suitable viscosity to ensured proper contact characteristics at the site of delivery. A preservative system composed of four parabens ensured that bioburden remained within acceptable limits. Sodium chloride was present to control osmolarity. The formula was slightly modified from the reconstitution solution used in the Phase 1 study in that Carbopol® 980 was added and the recommended storage changed from room temperature to refrigeration to maintain physical and chemical characteristics over a longer period of time. The batch formula for the reconstitution solution is presented in Table 5.

TABLE 5

| Ingredient | Quantity per batch (grams/80 kilograms) |
|---|---|
| Propylene Glycol USP | 4,000.00 |
| Sodium Chloride USP | 600.00 |
| Xanthan Gum, NF | 488.00 |
| Carbopol ® 980, NF | 96.00 |

TABLE 5-continued

| Ingredient | Quantity per batch (grams/80 kilograms) |
|---|---|
| Methylparaben NF | 13.12 |
| Propylparaben NF | 2.44 |
| Ethylparaben NF | 2.44 |
| Butylparaben NF | 2.44 |
| Hydrochloric Acid NF | — |
| Sodium Hydroxide NF | — |
| USP Purified Water | 74,795.57 |

Also, a matching placebo powder was formulated for Composition A using sucrose and pregelatinized corn starch as bulking agents. Colorants were added to match the dark green colour of Composition A. This mixture was lyophilized to mimic the granular appearance of Composition A. Sucrose also acted as a cryoprotectant and pregelatinized corn starch prevented undue moisture pick-up upon storage. The batch formula for the matching placebo powder is presented in Table 6.

TABLE 6

| Ingredient | Quantity per batch (g/2 kg) |
|---|---|
| XH2664 US Green 3 Shade* | 2.0 |
| FD&C Yellow No6 (E110) spray-dried | 6.2 |
| Sucrose, NF | 1659.8 |
| Pregelatinized Corn Starch, NF | 332.0 |
| Purified Water, USP | Removed during lyophilization |

*Contains FD & C Blue No 1 (E133) and FD & C Yellow No 5 (E102). The Certificate of Compliance with EC Directive 95/45/EC on Food Colours and the FAO/WHO specification can be found in Annex 4

The batch formula for the rectal enema that was administered in the Phase 2 study is presented in Table 7.

TABLE 7

| | Dose of Composition A to be administered | | | |
|---|---|---|---|---|
| Ingredient | 0 mg | 250 mg | 500 mg | 1000 mg |
| Reconstitution Solution* | 60 g | 60 g | 60 g | 60 g |
| Comp. A medicinal product | N/A | 250 mg | 500 mg | 1000 mg |
| Matching Placebo Powder** | 500 mg | N/A | N/A | N/A |

*See Table 6 for batch formula
**See Table 7 for batch formula

Reconstitution Solution 80 kg of reconstitution solution was prepared by pooling 4×20 kg bulk solutions. The manufacturing process for this preparation (20 kg bulk solutions and pooling) is presented below.

Step #1 Preparation of pH 2.5 USP Purified Water: 20 L Stainless steel vessel fitted with a mechanical stirrer was filled with 20 kg of USP Purified Water. A solution of HCl 1N is slowly added to the USP Purified Water under agitation to adjust the pH to 2.5±0.05.

Step #2 Preparation of the Xanthan Gum/Carbopol® Solution: A 20 L stainless steel double jacketed vessel fitted with a mechanical stirrer was filled with 11.1 kg of pH 2.5 USP Purified Water from Step #1 and the temperature was adjusted to 40° C. When the temperature reached 40° C., xanthan gum (122.0 g), sodium chloride (150.0 g) and Carbopol® 980 (24.0 g) were added and the solution was mixed at a speed of 800 rpm for 60 minutes.

Step #3 Preparation of the Preservatives Solution: A 1 L glass bottle containing 1000.0 g of propylene glycol was placed in a heated water bath to reach a temperature of 50° C. When the temperature reached 50° C., the 4 preservatives were added:

Methylparaben: 3.28 g

Propylparaben: 0.61 g

Ethylparaben: 0.61 g

Butylparaben: 0.61 g and the solution was kept under agitation at a temperature of 50° C. until the above preservatives were dissolved.

Step #4 Preparation of the bulk solution: The Preservatives Solution from Step #3 was added while mixing to the 20 L stainless steel vessel containing the Xanthan Gum/Carbopol® Solution prepared in Step #2 and maintained at a temperature of 40° C. USP Purified Water pH 2.5, from Step #1, was added to the vessel in sufficient quantity to reach 20.0 kg of bulk solution. Heating was stopped and the bulk solution was allowed to cool under agitation for 60 minutes. When a temperature of 25° C. was reached, the pH was measured and if necessary, adjusted to 6.5±0.05 using either HCl 1N or NaOH 1N solutions.

Steps #1 to #4 were repeated three times to generate 3×20 kg of additional bulk solutions.

Before proceeding with pooling, a viscosity test was performed on each of the 20 kg bulk solutions. If viscosity was between 1000 and 1200 cps, pooling proceeded (step #5).

Step #6 Packaging of the reconstitution solution: Not less than 60 g of reconstitution solution was filled using a metered pump in bottles with a cap fitted with a cannula.

Matching Placebo Powder

Step #1 Preparation of the Colour Solution: This solution was prepared by adding 2 g of US Green 3 Shade and 6.2 g of FD&C Yellow No 6 in a tared 1 L beaker equipped with a magnetic stirrer containing 6657.8 g of USP Purified Water; this solution was kept under agitation at 200 rpm for 5 minutes.

Step #2 Preparation of the Bulk Powder Dispersion: 1659.8 g of sucrose and 332.0 g of pregelatinized starch were mixed together in a 5000 mL beaker. This mixture was then slowly transferred, under agitation at 800 rpm, into the colour solution prepared in Step #1 and agitation was maintained until complete dispersion.

Step #3 Lyophilization: The resulting bulk powder dispersion from step #2 was transferred into freeze drying trays and initially dried at −50° C. for 24 hours. The product was then freeze-dried.

Composition A Rectal Enema

For each dose to be administered, patients received 2 bottles: one bottle containing the reconstitution solution and one bottle containing Composition A active substance or matching placebo powder. These bottles were kept under refrigeration.

For reconstitution, patients removed the 2 bottles described above from the refrigerator and left them at room temperature for 2 hours. Patients then reconstituted the rectal enema by transferring the content of the bottle containing the reconstitution solution to the bottle containing the Composition A active substance or matching placebo powder. Patients self-administered the rectal enema within 1 hour from reconstitution. The reconstituted enema was shaken manually for at least 30 seconds immediately before administration.

Example 3

Pre-Clinical Results Summary

Preclinical Studies

Numerous preclinical studies have been conducted demonstrating the anti-inflammatory, antioxidative, and immunomodulatory properties of Composition A. The preclinical studies include: (i) in vitro and in vivo pharmacology studies; and (ii) safety pharmacology and toxicology studies, and are summarized in Tables 8 and 9 below.

TABLE 8

Summary of In Vitro and In Vivo Pharmacology Studies Conducted with Comp. A

| Title of Study | Formulation/Route | Results/Findings |
|---|---|---|
| In Vitro Studies | | |
| Long-term Protection Against Lipid Peroxidation By Composition A in a Lipid Micelle Model In Vitro | N/A | Composition A significantly protected PLPC-Composition A micelles against lipid peroxidation with no apparent lag phase as seen with the classical anti-oxidants. (PLPC = 1-palmitoyl-2-linoleoyl-sn-glycro-3-phosphatidylchlorine) Anti-oxidative effect of Composition A was long-lasting, superior to that shown by Trolox over 24 hrs, and was maintained over 8 hrs while Trolox's was not. |
| Anti-oxidative Effect and Dose-Dependent Protection By Composition A of Hemolysis of Human and Bovine Erythrocytes Exposed to 1 to 3 mM tBHP | N/A | Composition A protected erythrocytes against hemolysis and lipid peroxidation in a dose-dependent manner. The greater the damage by ROS, the greater the protection by Composition A - as observed in the micelle model; and Composition A exhibited a long-lasting effect. |
| In Vitro Modulation of Cytokine Expression in Alveolar Macrophages (AM) by Composition A | N/A | Composition A pretreatment of lipopolysaccharide (LPS)-stimulated AM reduced TNF-$\alpha$ (at 18-24 h) and increased IL-10 (at 72-96 h) production at both protein and mRNA levels in a concentration- and time-dependent manner; and significantly reduced the TNF-$\alpha$/IL-10 ratio produced by LPS-stimulated AM - demonstrating its strong anti-inflammatory properties. TNF-$\alpha$/IL-10 ratio was further reduced when Composition A was used in combination with budesonide or beclomethasone - indicating it potentiates the effects of other anti-inflammatory agents. |
| Effects of Composition A on Anti-inflammatory Functions of Isolated Human Blood Neutrophils | N/A (0.2% highest Conc)- | In isolated human neutrophils stimulated by A23187 ionophore, Composition A pretreatment showed: A 75% reduction in leukotrienes at the highest dose (0.2%), as well as a 85% reduction in superoxide anion, and 50% inhibition of neutrophil degranulation. In addition, Composition A decreased the production of IL-1$\beta$ and IL-8; and inhibited 5-lipooxygenase (LO) enzyme, phagocytosis and intracellular calcium mobilization. These effects may reveal the important mechanisms of Composition A's anti-inflammatory properties. |
| Composition A, a Novel Modulator of Pro- and Anti-inflammatory Cytokine Production: Effect on Th1/Th2 Cytokine Profile. | N/A (0.05 to 0.1% - low; 0.2% - high Conc.) | In isolated human peripheral blood mononuclear leucocytes (PBML): Composition A alone at low concentrations (0.05%) increased the spontaneous production of the Th2 cytokines - IL-5 and IL-13; and TNF-$\alpha$ production by 937 monocytoid cells at 0.1% concentration. At the higher 0.2% concentration, Composition A inhibited the spontaneous and stimulated generation of both Th1 and Th2 cytokines. These results suggest that at higher concentrations, Composition A could modulate the abnormal deviation between the Th1 and Th2 cytokines generated by immune cells in pathologic conditions. |
| In Vivo Studies | | |
| Correction of Cytokine Imbalance By Composition A in Dextran Sulfate Sodium (DSS)-Induced Colitis in Rats | Intrarectal (IR) and Intraperitoneal (IP) (2.5 & 5 mg/kg doses) | Composition A attenuated DSS-induced colitis in rats, reflected by a dramatic 75% reduction of colon weight-to-length ratio at the 2.5 mg/kg dose, regardless of whether administered IR or IP. The reduced inflammation was correlated with reduction in mucosal TNF-$\alpha$ (30% & 50% for the 2.5 & 5 mg/kg Composition A doses, respectively) and IL-1$\beta$ levels (64% & 68% for the 2.5 & 5 mg/kg Composition A doses, respectively) compared to untreated rats. A significant 75% and 50% reduction in the plasma TNF-$\alpha$ and IL-1$\beta$ levels, respectively, was also observed. |

TABLE 8-continued

Summary of In Vitro and In Vivo Pharmacology Studies Conducted with Comp. A

| Title of Study | Formulation/Route | Results/Findings |
| --- | --- | --- |
| Correction of Cytokine Imbalance By Composition A in 2, 4, 6, Trinitrobenzene Sulfonic Acid (TNBS)-Induced Colitis in Rats | Intrarectal (IR) and Intraperitoneal (IP) (2.5 mg/kg dose) | Pretreatment with Composition A - 2.5 mg/kg IR or IP reduced weight/length ration of the colon by 33% compared to a 50% increase in the non-treated (saline) rats. A 65% reduction in the macroscopic score used to assess colonic mucosal damage was also observed. As in the DSS-induced colitis model, similar results were obtained by the IR or IP routes. |
| Anti-inflammatory Effect of Composition A in the Rat Paw Edema Model (Carrageenan Model) | Intraperitoneal (IP) (0.5, 5 & 50 mg/kg doses) and Oral (50 mg/kg dose) | Intraperitoneal Composition A pretreatment and administration simultaneously with carrageenan injection into the right paw of rats dose-dependently reduced paw thickness - 70% reduction with 50 mg/kg dose and 60% reduction with the 5 mg/kg dose. Similar results were obtained with the oral Composition A - 50 mg/kg dose compared to the IP route of administration - suggesting a high oral bioavailability of Composition A. |
| Anti-inflammatory Effects of Composition A in Transgenic Rats Expressing HLA-B27 With Spontaneous Inflammatory Disease | Oral (50 mg/kg dose)- | In transgenic rats expressing HLA-B27 phenotype and followed for 45 weeks until they developed a full-blown inflammatory disease, Composition A - 50 mg/kg administered in a single oral dose daily for 8 weeks: Significantly reduced fecal blood, an index of colitis; reduced psoriatic plaques; and increased body weight in all animals. However, it is noteworthy that the study was not well-controlled. |
| Evaluation of the Immunogenicity and Cytotoxicity of Composition A | Oral (up to 50 mg/kg in rats) Cream/Topical (5% in mice & man) (1% in albino rabbits) | Composition A did not induce any IgE immune response. No cytotoxicity was observed at doses up to Composition A - 50 mg/kg (oral liquid) in rats; following topical administration of 5% Composition A cream in mice and man; and Composition A cream 1% in albino rabbits. |

TABLE 9

Summary of Safety Pharmacology and Toxicology Studies Conducted With Comp. A

| Study Title | Results/Findings |
| --- | --- |
| Safety Pharmacology Studies | |
| A Respiratory Safety Pharmacology Study in Conscious Sprague-Dawley Rats following a Single Oral Administration. | No treatment-related adverse effects on respiratory functioning or clinical condition. |
| A Functional Observational Battery (FOB) Neurological Assessment in the Sprague-Dawley Rat Following a Single Oral Administration. | No treatment-related pharmacologically significant effect on the behavior of rats. |
| Cardiovascular Oral Study in Minipigs using Telemetry. | No treatment-related changes in cardiovascular parameters, clinical signs, body weight or food consumption. |
| ICH Battery of 3 Genetic Toxicology Studies | |
| Bacterial Mutagenicity Assay (AMES Test). In-Vitro Mammalian Chromosomal Aberration Test. In-Vivo Mouse Micronucleus Test. | All 3 studies were negative - indicating Composition A was not mutagenic, did not cause any chromosomal aberrations, and was not genotoxic, respectively. |
| Reproductive Toxicology Studies | |
| Oral Gavage Developmental Toxicity Study in the Hannover Wister Rat (Segment II). Oral Gavage Dose Range Finding Developmental Toxicity Study in the Rabbit (Segment II). Oral Gavage Development Toxicity Study in the Rabbit (Segment II). | In all 3 studies, Composition A administration was not associated with any maternal or fetal toxicity or teratogenic effects. |
| General Toxicology Studies - Oral in Rats | |
| A Maximum Tolerated Dose and 21-Day Range-Finding Oral Toxicity Study in Sprague Dawley Rats. 6-Month Oral Gavage Toxicity Study in Sprague-Dawley Rats. | All doses were well tolerated. No maximum tolerated dose was identified in the dosage range tested. No treatment-related deaths, clinical signs or findings, organ weight differences, gross morphologic or histopathological findings. |
| General Toxicology Studies - Oral in Minipigs | |
| Oral Single-Dose (Dose Range Finding) and 14-Day Repeat-Dose Exploratory Toxicity Study in Minipigs. 3-Month Oral Repeat-Dose Toxicity Study in Minipigs. | All doses were well tolerated. No maximum tolerated dose was identified in the dosage range tested. No treatment-related deaths, clinical signs or findings, organ weight differences, gross morphologic or histopathological findings. |

TABLE 9-continued

Summary of Safety Pharmacology and Toxicology Studies Conducted With Comp. A

| Study Title | Results/Findings |
|---|---|
| General Toxicology Studies - Intrarectal in Minipigs | |
| An Intrarectal Single-Dose (Dose Range Finding) and 14-Day Repeat-Dose Exploratory Toxicity Study in Minipigs. 12-Week Intrarectal Repeat-Dose Toxicity Study in Minipigs Followed by a 2-Week Recovery Period. | All doses were well tolerated. No maximum tolerated dose was identified in the dosage range tested. No treatment-related deaths, clinical signs or findings, organ weight differences, gross morphologic or histopathological findings. |
| General Toxicology Studies - Dermal in Minipigs | |

Example 4

Phase 1 Clinical Trials in Ulcerative Colitis

Following the positive results obtained with Composition A in preclinical studies, it was developed as a treatment for active mild-to-moderate distal ulcerative colitis. This led to the conduct of the first-in-man clinical trial in Germany, a Phase I safety clinical trial in normal human volunteers. We therefore obtained the necessary regulatory approval.

The Phase 1 study was a randomized, double-blind, parallel-group, single-ascending dose, placebo-controlled safety and tolerability study performed in 24 healthy human volunteers assigned to four different cohorts. The doses ranged from 187.5 mg/60 g to 1500 mg/60 g of rectal enema or placebo.

The study showed no clinically relevant changes in vital signs (blood pressure, pulse rate, body temperature and respiratory rate) or electrocardiogram (ECG), no clinically significant abnormalities, no adverse events deemed related to the investigational medicinal product, and no signs of ulceration, erosion, or edema in the rectal mucosa when sigmoidoscopies were performed 8 to 10 hours after dosing.

Our conclusions from this study were as follows: Administration of up to 1500 mg/60 g of Composition A rectal enema was safe and very well tolerated. There were no clinically significant findings in any measurements, and no clinically relevant changes were observed from the pre-dose to the post-dose examinations. In addition, a maximum tolerated dose was not identified in the dosage range studied.

Safety Evaluation
Extent of Exposure

All 24 subjects included in the study received a single dose of Composition A rectal enema or placebo: eight subjects were treated with placebo; four subjects each received a single dose of 187.5 mg, 375 mg, 750 mg or 1500 mg Composition A rectal enema.

Brief Summary of Adverse Events

None of the subjects reported baseline AEs and only one subject out of the 24 subjects included in the study (4.2%) reported one AE after treatment.

Analysis of Adverse Events

For Subject 004 (placebo) a mild thrombophlebitis was reported which started on Day 3 and resolved completely within 8 days. Relationship to the study medication was rated as unrelated by the investigator.

Deaths, Other Serious Adverse Events and Other Significant Adverse Events

There were no deaths, other SAEs or other significant AEs. None of the subjects dropped out from the study due to an AE.

Clinical Laboratory Evaluation
Listings of individual laboratory measurements by subject and each abnormal laboratory value
Evaluation of Each Clinical Laboratory Parameter
Clinical Laboratory Values Over Time Most clinical laboratory values were within the normal range. Individual deviations from the normal range were seen for a number of parameters. Most of these deviations were normal fluctuations usually observed in healthy subjects (very slight deviations from the normal range, mostly within the accuracy of the method, often already present prior to study drug administration).

A decrease in hemoglobin and hematocrit was observed in several subjects; this can be attributed to the numerous blood samplings performed in this study.

On examining the differential blood count abnormal values were seen above and below the normal range without any consistent treatment-related changes. However, it should be taken into account that the differential blood count is known to be very susceptible to artifacts.

Subject 024 (1500 mg) showed an isolated increase in AST from 28.6 U/L at screening and 34.2 U/L at check-in on Day 1 to a maximum of 72.8 U/L on Day 3 (normal range 48 U/L). Thereafter, AST decreased and was again within the normal range on Day 8 (47.0 U/L). No other liver function parameters showed any increase. The increase was less than twice the upper limit of the normal range and was considered as not clinically significant by the investigator. No other subject showed any remarkable changes in liver function parameters.

Stool investigations for parasites, ova, bacterial culture and toxins were all negative. All haemoccult tests were negative.

Individual Clinically Significant Abnormalities

There were no clinically significant clinical laboratory test results.

Vital Signs, Physical Findings and Other Observations Related to Safety
Blood Pressure and Pulse Rate Mean vital sign measurements are displayed in FIG. 3A-E.

There was no clinically significant time- or dose-related changes in mean vital signs. Overall, mean vital signs decreased after dosing in all treatment groups, which can be attributed to diurnal changes (dosing performed in the evening at bedtime).

There were some abnormal individual values outside the normal range, but the frequency of abnormal values did not increase with dose. For most parameters, values below and above the normal range were seen; the lowest frequency of abnormal values was observed after the highest dose of Composition A, except for pulse rate, where four low values were detected in subjects in the 1500 mg group (all observed in subject 019: 40 to 43 beats/min at 0.25 to 1 hour after dosing; the subject had already 42 beat/min at check-in) compared to 0 to 1 beat/min change from the pre-dose value in the other treatment groups. Most abnormal values were observed for respiratory rate, but for young healthy subjects a respiratory rate below 15/min at rest is not uncommon.

Example 5

Phase 2a Clinical Trial in Ulcerative Colitis

Next, after receiving approval from regulatory authorities for the first-in-patient (Phase 2a) study, we conducted a two-week, exploratory randomized, double-blind, parallel-group, dose-ranging, placebo-controlled safety, tolerability, biomarker and efficacy clinical study of Composition A rectal enema in patients with active mild-to-moderate distal ulcerative colitis.

Findings from this short, two-week study can be summarized as follows. The primary objective of this study was met. Administration of 250 mg, 500 mg and 1000 mg doses of Composition A rectal enema once daily was safe and well tolerated in subjects with active mild-to-moderate distal ulcerative colitis. These results are consistent with the results of the preceding Phase 1 study, in which single ascending doses of Composition A rectal enema from 187.5 to 1500 mg were safely and tolerably administered to healthy volunteers and a maximum tolerated dose was not observed.

The following sections present some of the important results of Composition A treatment in patients with active mild-to-moderate distal ulcerative colitis, as observed in the Phase 2a study.

Safety Results

Administration of all 3 doses of Composition A rectal enema (250 mg, 500 mg and 1000 mg) once daily was safe and well tolerated in subjects with active mild-to-moderate distal ulcerative colitis. Overall, there were no treatment-related or serious adverse events or deaths during the study, no withdrawals due to adverse events, and there were no clinically relevant time- or treatment-related changes in the laboratory parameters, ECGs and vital signs.

Biomarker Results

Figure 4:
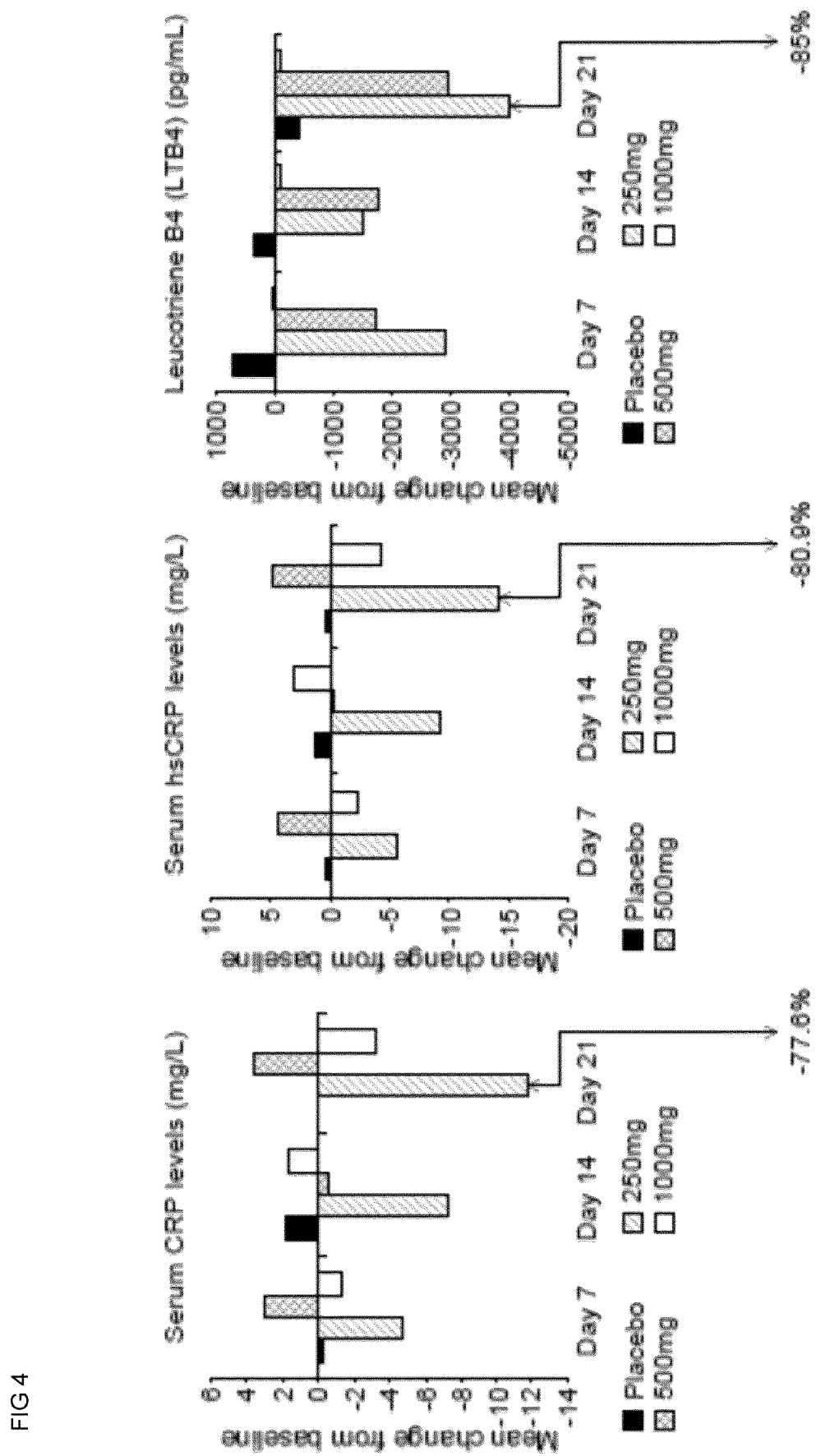
FIG. 4. Mean change from baseline in the levels of inflammatory biomarkers in patients with active mild-to-moderate distal ulcerative colitis.

As shown in FIG. 4, marked, consistent biomarker reductions of 29 to 63.6% in serum C-reactive protein (CRP), high sensitivity-CRP (hs-CRP), erythrocyte sedimentation rate (ESR), fecal calprotectin (FC), and fecal lactoferrin (FL), in response to 2 weeks of Composition A 250 mg treatment (at endpoint), along with further reductions to 77.6, 80.9 and 82.9%, respectively, in CRP, hs-CRP and FL levels (250 mg: p<0.03; 1000 mg: p<0.04) by Day 21, compared with overall 18.8 to 120% increases in the placebo group over the 21 days, are objective evidence of the drug's biological activity on intestinal inflammation in ulcerative colitis.

Further objective evidence of the biological activity of Composition A rectal enema on intestinal inflammation in ulcerative colitis included marked reductions in serum Leukotriene $B_4$ ($LTB_4$) levels in the Composition A 250-mg treatment group. At the Day 14 visit, the levels were reduced by 31.4%, while those in the placebo group had risen by 29%. (By Day 21, the levels in the Composition A-250 mg treatment group had fallen by 85.0%.). Smaller reductions in serum $LTB_4$ levels were also observed in the 500 mg and 1 000 mg Composition A treatment groups (28.0% and 22.2%, respectively). These findings are consistent with the results of earlier animal pharmacology studies which demonstrated that Composition A reduces the production and release of lipid mediators of inflammation, including prostaglandins and leukotrienes.

Figure 5:
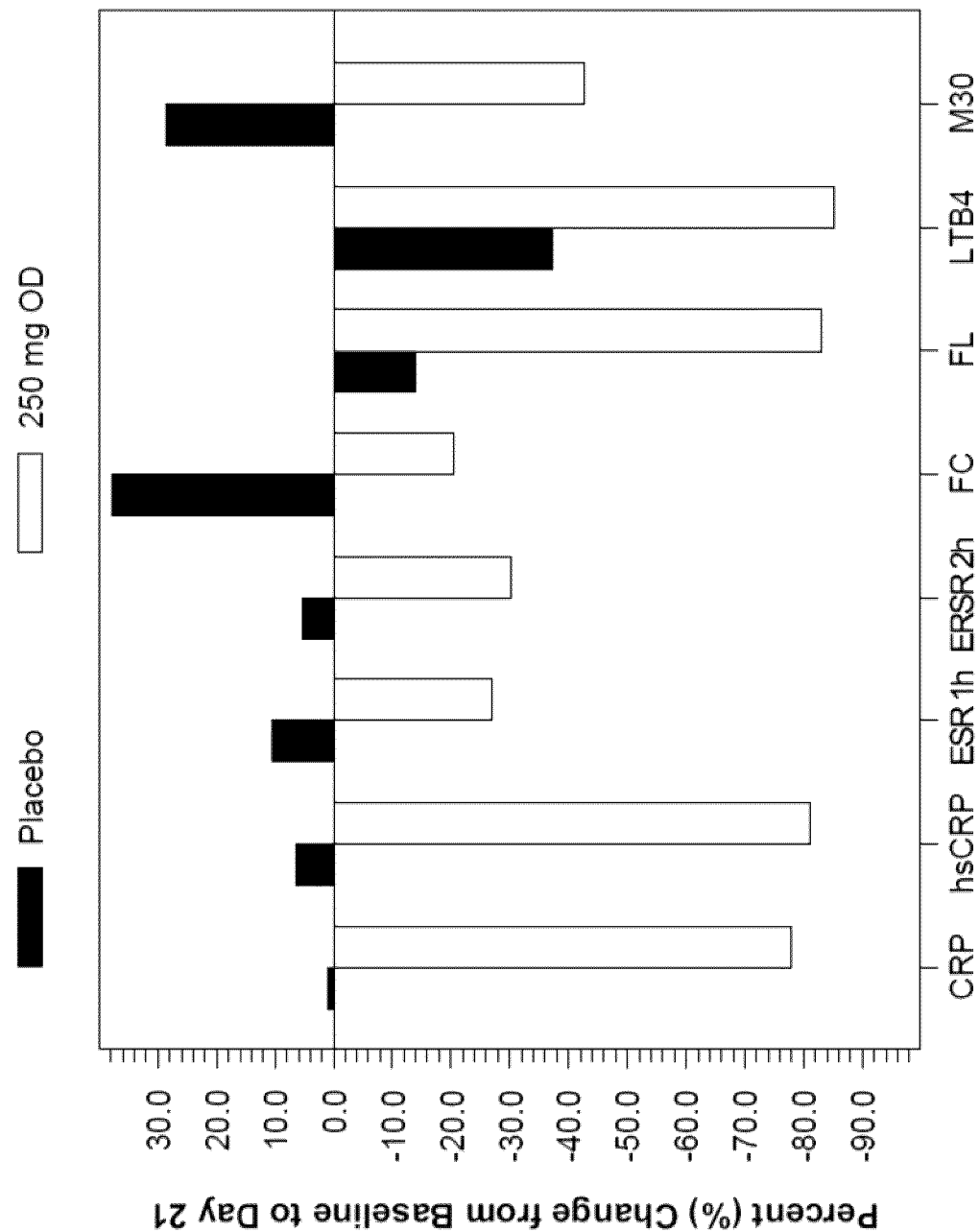
FIG. 5. Mean change from baseline in the levels of inflammatory and ulcerative colitis biomarkers (hsCRP, M30 apoptosome, LTB4, etc.) 7 days after termination of treatment with Composition A—250 mg (once daily for 14 days). CRP: serum C-reactive protein; hsCRP: serum high sensitivity CRP; ESR: erythrocyte sedimentation rate; FC; fecal Calprotein; FL: fecal Lactoferrin; LTB: serum Leukotriene B; M30: change from baseline to day 14 in M30 Apoptosome level in biopsy tissue.

Yet more objective evidence of Composition A's biological activity was the 42.5% reduction in the concentration of M30 apoptosome (a biomarker of apoptosis) in colonic mucosal biopsy tissue from patients receiving 250 mg and 500 mg treatments of Composition A, compared with an increase of 28.6% in the placebo group (FIG. 5).

The lack of a dose-response in the results obtained for the measured efficacy and biomarker parameters is consistent with the results obtained previously in studies conducted with approved first-line treatments for mild-to-moderate distal UC—the rectal and oral 5-aminosalicylates as well as the biologicals (for moderate-to-severe UC)—that did not also demonstrate a consistent dose-response relationship.

The data presented herein indicate that the thylakoid extract (Composition A medicinal product) of the present invention was active against ulcerative colitis.

Interestingly, in addition the intestinal-specific marker: fecal lactoferrin, two general inflammation biomarkers the C-reactive protein (CR) and high sensitivity C-reactive protein (hs CRP) were also markedly decreased upon treatment (see FIG. 5).

Example 6

Thylakoids Against Cardiovascular Diseases

The role of inflammatory in the propagation of atherosclerosis and susceptibility to cardiovascular events is well established. Inflammation is central to the initiation and progression of atherothrombosis and triggering cardiovascular disease events. Of the wide array of inflammatory biomarkers that have been studied, high-sensitivity C-reactive protein (hsCRP) has received the most attention for its use in screening and risk reclassification.

Particularly, hsCRP has been implicated in a variety of cardiovascular diseases and peripheral artery diseases such as: stroke, myocardial/cerebral infraction, atherosclerosis, bypass surgery or ischemia reperfusion injury.

Multiple studies suggest the association of low-level chronic inflammation during atherogenesis and demonstrate that CRP is a risk predictor of cardiovascular disease. High sensitivity C-reactive protein is associated with the buildup of cholesterol and other fatty material in the coronary arteries. CRP is an acute phase reactant produced by the liver, strongly regulated by IL-6 concentrations.

In 2003, the Centers for Disease Control and Prevention and the American Heart Association (AHA) recommended that CRP could be used as a global assessment of cardiovascular risk. Other national and medical agencies have followed and recommended this CRP assessment in patient at intermediate risk for a cardiovascular event: in 2009 for the Canadian Cardiovascular Society and the National Academy of Clinical Biochemistry Medicine Practice Guidelines and in 2010 for the American College of Cardiology Foundation-AHA.

The Emerging Risk Factors Collaboration (2012) has evaluated 52 prospective cohort studies including more than 245 000 individual records of people without a history of cardiovascular disease to quantify the improvement in the prediction of a first cardiovascular event when the assessment of circulating CRP or fibrinogen was added to the assessment of risk factors used in standard risk scores. They concluded that the additional assessment of CRP or fibrinogen in people at intermediate risk for a cardiovascular event could help prevent one additional event over a period of 10 years for every 400 to 500 people so screened.

FDA has approved CRESTOR (rosuvastatin) for primary prevention of cardiovascular disease (FDA News Release 2010) based on the recommendation of an FDA advisory panel (Memorandum 2012). Crestor became the first statin to receive this indication and the first to include an indication based on the biomarker high sensitivity C-reactive protein. Crestor was already approved for use in combination with diet and exercise to lower LDL cholesterol triglycerides in patients with a high amount of these substances in their blood. The medication is also approved to slow the progression of atherosclerosis (Memorandum 2012).

The FDA advisory panel recommended this new indication for Crestor on results obtained from a trial called the Justification for the Use of statins in Prevention: an Intervention Trial Evaluation Rosuvastatin (JUPITER). The JUPITER trial has been performed because it has been observed that statin therapy results in a greater clinical benefit when levels of the inflammatory biomarker C-reactive protein (CRP) are elevated and that statins lower CRP levels in a manner largely independent of LDL cholesterol levels. These findings, along with basic laboratory evidence, have led to the hypothesis that statins may also have anti-inflammatory properties that are important for prognosis and treatment. If so, then the level of CRP achieved as a result of statin therapy may have analogous clinical relevance (Ridker et al., 2005).

The JUPITER trial compared the safety and the effectiveness of CRESTOR 20 mg versus placebo in the time to first occurrence of cardiovascular events (cardiovascular death, nonfatal heart attack, nonfatal stroke, hospitalization for unstable angina, and arterial revascularization). This trial included approximately 18,000 individuals with no clinically evident heart disease and low-density lipoprotein (LDL) cholesterol levels below 130 mg/dL. The overall trial results showed that CRESTOR-treated individuals had a lower risk of suffering a major cardiovascular event compared to individuals receiving a placebo, with a 44% (P<0.00001) relative reduction in risk. Based on these results, the JUPITER trial was stopped early after only two years while it was designed for a three or four-year trial (Memorandum, 2012).

The new indication for CRESTOR would be for men 50 or older and women 60 or older who have fasting LDL of less than 130 mg/dL, a high sensitivity CRP of 2.0 mg/L or greater, triglycerides of less than 500 mg/dL, and no prior history of heart attack or stroke, or coronary heart disease risk.

It therefore seems sound to predict that individuals at risk of developing chronic inflammation diseases or disorders (i.e. presenting high levels of hsCRP marker) may profit from a prophylactic regimen of Composition A to diminish their risk of progression to acute symptoms, or delay onset of disease.

Example 7

In Vitro Detection of Anti-Inflammatory Activity in Thylakoid Extracts by Inhibition of Nitric Oxide (NO) Produced by iNOS In vitro anti-inflammatory activity of thylakoid extracts was assessed by testing their capacity to inhibit nitric oxide (NO) produced by the inducible nitric oxide synthase (iNOS). NO is synthesized by 4 nitric oxide synthases (NOS) through a series of redox reactions. These are endothelial nitric oxide synthase (eNOS), inducible nitric oxide synthase (iNOS), neuronal nitric oxide synthase (nNOS) and mitochondrial nitric oxide synthase. The enzymes eNOS and nNOS are constitutively expressed in cardiomyocytes, while iNOS is elevated in the myocardium of patients with heart failure. iNOS is therefore associated cardiovascular diseases such as atherosclerotic plaque progression and ischemia-reperfusion injury.

Figure 6:
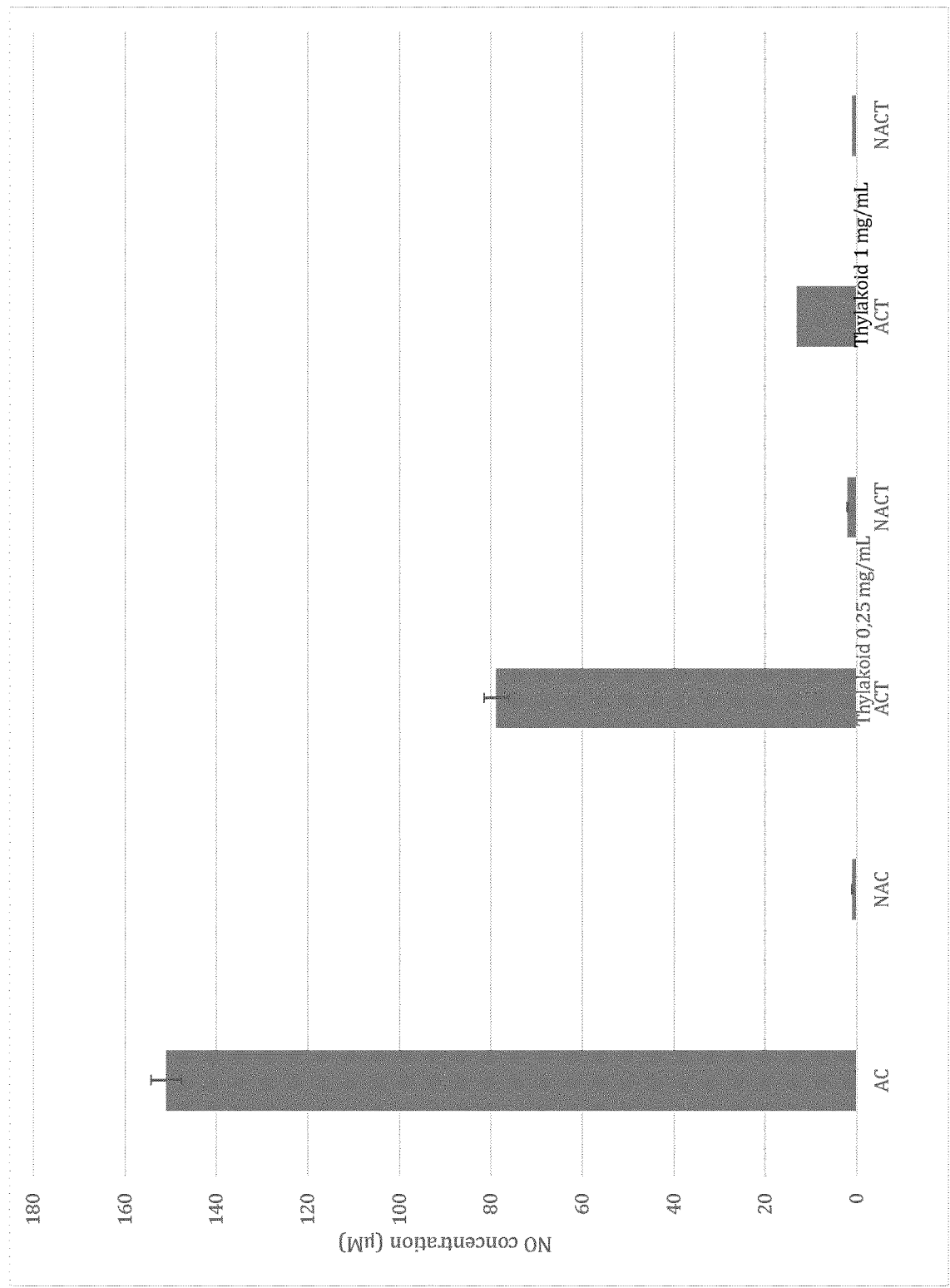
FIG. 6. Inhibition of NO by functional thylakoid extract through iNOS pathway. AC: activated RAWb264.7 cells (control), NAC: Non-activated cells, ACT: activated cells pretreated with thylakoids at 0.25 mg/mL or 1 mg/mL, NACT: non-activated cells pretreated with thylakoids at 0.25 mg/mL or 1 mg/mL.

An in vitro study realized with thylakoid extracts has shown that they can inhibit iNOS therefore decreasing harmful NO activity (FIG. 6).

Experimental Conditions

Thylakoids

Thylakoids were tested for their effect on NO production through iNOS pathway. Thylakoid powder was suspended at 5 mg/mL in Hank's buffer.

Murine Cell Culture

Murine macrophage-like RAW 264.7 cells are one of the most widely used cell lines to investigate the function and differentiation of monocytes and macrophages in response to various inflammatory mediators. RAW 264.7 is a macrophage-like cell model which produce large amount of NO through iNOS pathway in response to INFγ, TNFα (Chan and Riches, 2001; Koide et al., 2007).

In this experiment, RAW 264.7 cells were maintained in RPMI-1640 medium supplemented with 10% heat-inactivated bovine serum containing 1 mM sodium pyruvate, 10 mM HEPES and 50 µg/mL gentamycin. The cells were maintained at 37° C. in a moisture-saturated atmosphere containing 5% $CO_2$.

Evaluation of NO Production Through iNOS Pathway by the Griess Reagent Method:

RAW 264.7 cells ($25 \times 10^3$ cells/well) were pretreated 24 h with various reconstituted thylakoid extracts at concentrations of 0.25 mg/mL or 1 mg/mL. After pretreatment, cells were washed twice with 10% FBS RPMI-1640 and then iNOS was stimulated to produce NO for a period of 24 h by activation with 100 ng/ml of lipopolysaccharides (LPS) and 10 ng/mL of cytokine interferon gamma (INFγ). NO production was measured using the Griess reagent method involving the detection of nitrite ions ($NO_2^-$) formed by the spontaneous oxidation of NO under physiological conditions. Equal volumes of sulfanilic acid and N-(1-naphthyl) ethylenediamine were mixed together to form the Griess reagent. The reaction is described as: in presence of $NO_2^-$, sulfanilic acid is converted to a diazonium salt, which in turn is coupled to N-(1-naphthyl) ethylenediamine to produce a pink coloration that is measured at 548 nm. NO concentration is expressed in µM.

It can be observed in FIG. 6 that activated cells produce 150 µM of NO induced by iNOS. This production is reduced to 80 µM (47% reduction) and 15 µM (90% reduction) of NO when cells are treated with 0.25 mg/mL and 1 mg/ml of thylakoids, respectively. As control, pre-treatment of non-activated cells did not show any effect with any thylakoids extract concentrations.

Measurement of Antioxidant Capacity of Thylakoid Extracts

Over the last two decades, it has been demonstrated that reactive oxygen species (ROS), including free radicals, are involved in cardiovascular diseases (Jawalekar et al, 2010, Zhang et al., 2014). Myocardial redox imbalance is a characteristic of this syndrome because reactive oxygen and nitrogen reactive species can behave as signaling molecules in the pathogenesis of hypertrophy and heart failure, resulting in a dysregulation of cellular calcium handling, contractile machinery (Arcaro et al., 2015). The importance of ROS has been underlined in several studies:

ROS are important intra-neuronal signaling intermediates in angiotensin II (AngII)-related neuro-cardiovascular diseases associated with excessive sympatho-excitation, including hypertension and heart failure (Zimmerman 2011).

The levels of oxidative lipid damage is an early predictor of development of cardiovascular disease (CVD) (Zhang et al, 2014). The subcellular changes in the equilibrium in favor of free radicals can cause increase in the oxidative stress which leads to cardiomyopathy, heart attack or cardiac dysfunction (Zhang et al, 2014).

In a clinical study with patients with cardiovascular diseases, it was demonstrated that total antioxidant capacity was reduced (Jawalekar et al., 2010). These results support that failure of antioxidant defense mechanism against oxidative stress may be an important factor in the pathogenesis of cardiovascular diseases.

Figure 7:
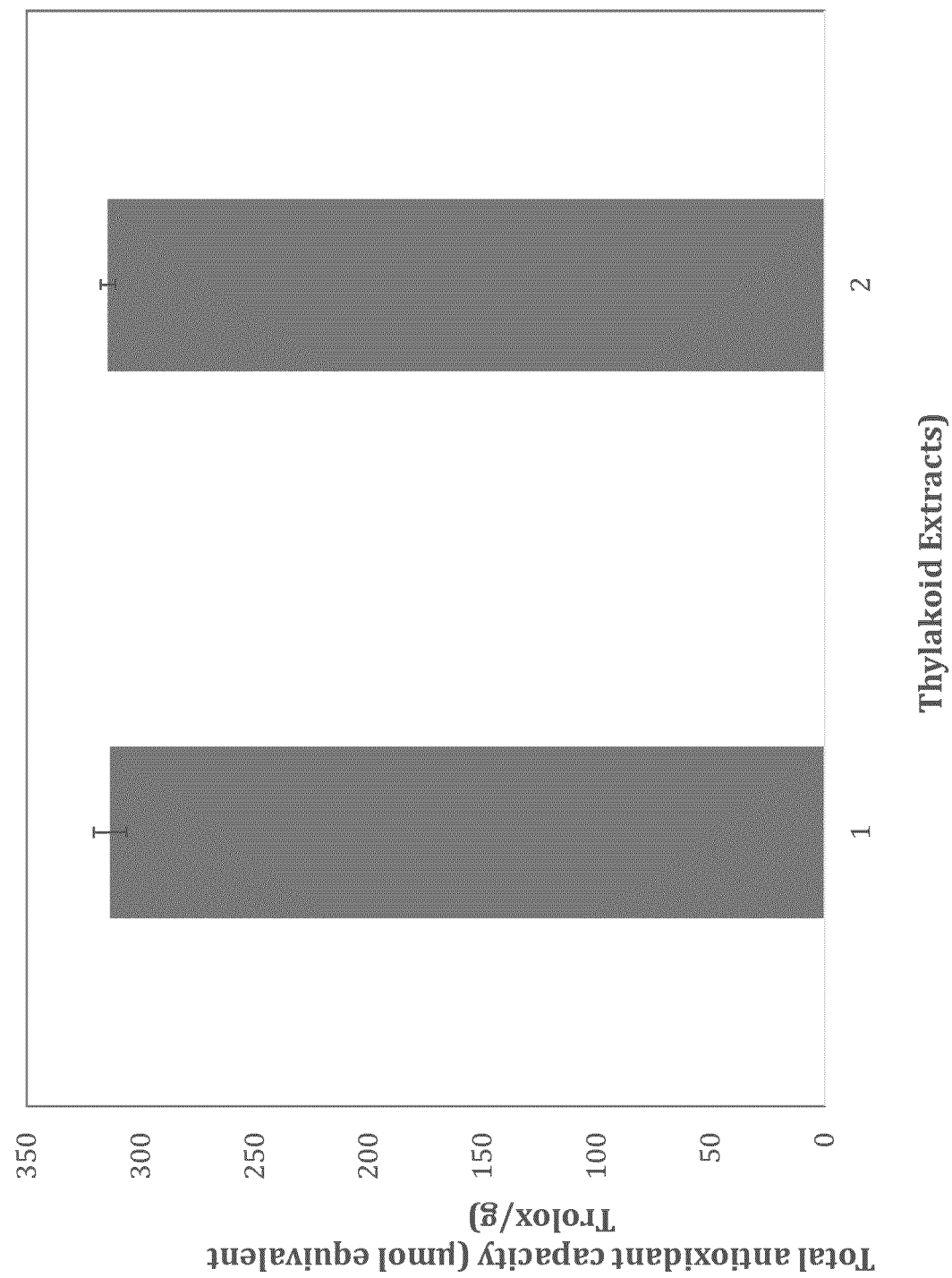
FIG. 7. Antioxidant capacity of functional thylakoid extracts obtained by ORACFL test.

The total antioxidant capacity of thylakoids was assessed by ORACFL assay (FIG. 7).

ORACFL Assay:

Fluorescein was used as fluorescent probe and 2,2'-azobis (2-amidino propane) dihydrochloride (AAPH) as generator of peroxyl radicals (Wu and al, 2004). The results of antioxidant capacity are defined in relation to the antioxidant capacity of a reference molecule, Trolox.

Preparation of Samples

In two assays, one (1) gram of thylakoids was mixed with hexane/dichloromethane (1:1 Hex/Dc), followed by acetone/water/acetic acid (70/29.5/0.5). Fractions Hex/Dec were dried under nitrogen atmosphere in a water bath at 30° C., and the residue was reconstituted with 10 ml of acetone: water, containing B-Cyclodextrin. After centrifugation, the supernatant was used to measure ORACFL following further dilution with assay buffer, if necessary. The hydrophilic fractions were transferred into a volumetric flask of 25 ml and diluted with 25 ml acetone/water/acetic acid (70/29.5/0.5) and ORACFL was performed. Each sample was extracted and tested in duplicate.

ORAC assays were performed on a FLUOstar Galaxy plate reader. The final ORACFL values were calculated using a quadratic regression equation (y=ax2+bx+c) between Trolox or sample concentration and the net area under the fluorescein decay curve. Data were expressed in micromoles equivalent Trolox (ET) per gram of sample (µmol ET/g).

The results (FIG. 7) demonstrate the total antioxidant capacity of 2 samples of thylakoid extracts by ORACFL assay. The results show that one gram of thylakoids has the same antioxidant capacity as 300 µmol of Trolox in both extracts.

Superoxide Dismutase Activity of Thylakoids

Reactive oxygen species (ROS) are free radical derivatives of oxygen. The best-known ROS include superoxide anion ($O_2^-$), hydrogen peroxide ($H_2O_2$) and the hydroxyl radical (OH—). Superoxide dismutase (SOD) is the antioxidant enzyme scavenging superoxides ($O_2^-$) and producing $H_2O_2$ at the end of the reaction.

Superoxides play important roles in the pathogenesis of many cardiovascular diseases, including hypertension and atherosclerosis (Fukai and Fukai, 2011). SODs also play a critical role in endothelial and mitochondrial function by inhibiting oxidative pathway of bioavailable NO (Fukai and Fukai, 2011). The expression of SOD is decreased in myocardial infarction (MI)-induced failing heart (van Deel et al., 2008).

Dysregulation of SOD's pathways leads to endothelial dysfunction, altered vascular tone, vascular inflammation, vascular remodeling, enhanced vascular permeability, and increased platelet aggregation, which contribute to many cardiovascular diseases. SOD plays an important role in protecting the heart against oxidative stress and myocardial infraction. As well, restoring or providing an active SOD could therefore plays a critical role in cardiovascular diseases.

Thylakoids extracts were therefore assessed for their SOD activity.

Experimental Conditions for SOD Activity in Thylakoids

SOD activity was assayed using photo-oxidation of riboflavin as a ROS-generating reagent. This activity was assayed by the ability of thylakoids to inhibit photochemical reduction of Nitro Blue Tetrazolium (NBT) at 560 nm (Kuo et al., 2013; Beauchamp and Fridovich, 1971). Reduction of NBT to a blue formazan occurs via an intermediate radical (NBTH.) from which the colored compound is produced by superoxides (when riboflavin is added and light turns on). By scavenging superoxides, SOD inhibits this reaction resulting in the reduction of the coloration.

Two Thylakoids extracts (0.1 g) were suspended in 10 mL of buffer (50 mM potassium phosphate buffer (pH 7.8), 1 mM EDTA and 2% (w/v) PVPP). The suspension was centrifuged 30 min at 14 000 rpm and 4° C. The supernatant was taken for the SOD assay.

The reaction mixture for the SOD assay contained: 20 µL of the supernatant, 1.3 mL of assay buffer (50 mM K—$PO_4$ buffer (pH 7.8), 1 mM NBT, 500 mM L-methionine, 10 mM EDTA and 2.5% (v/v) Triton,). This mixture was kept in the dark until the assay substrate, riboflavin (0.2 mM) was added. The reaction started by illuminating the reaction mixture containing riboflavin with a luminescent lamp 5 minutes at room temperature. The sample was then read at 560 nm. A standard curve with bovine SOD was used (SOD enzymatic units over % activity) to determine the SOD activity of the different thylakoid extracts. Protein contents in thylakoids were determined by Bradford method.

Figure 8:
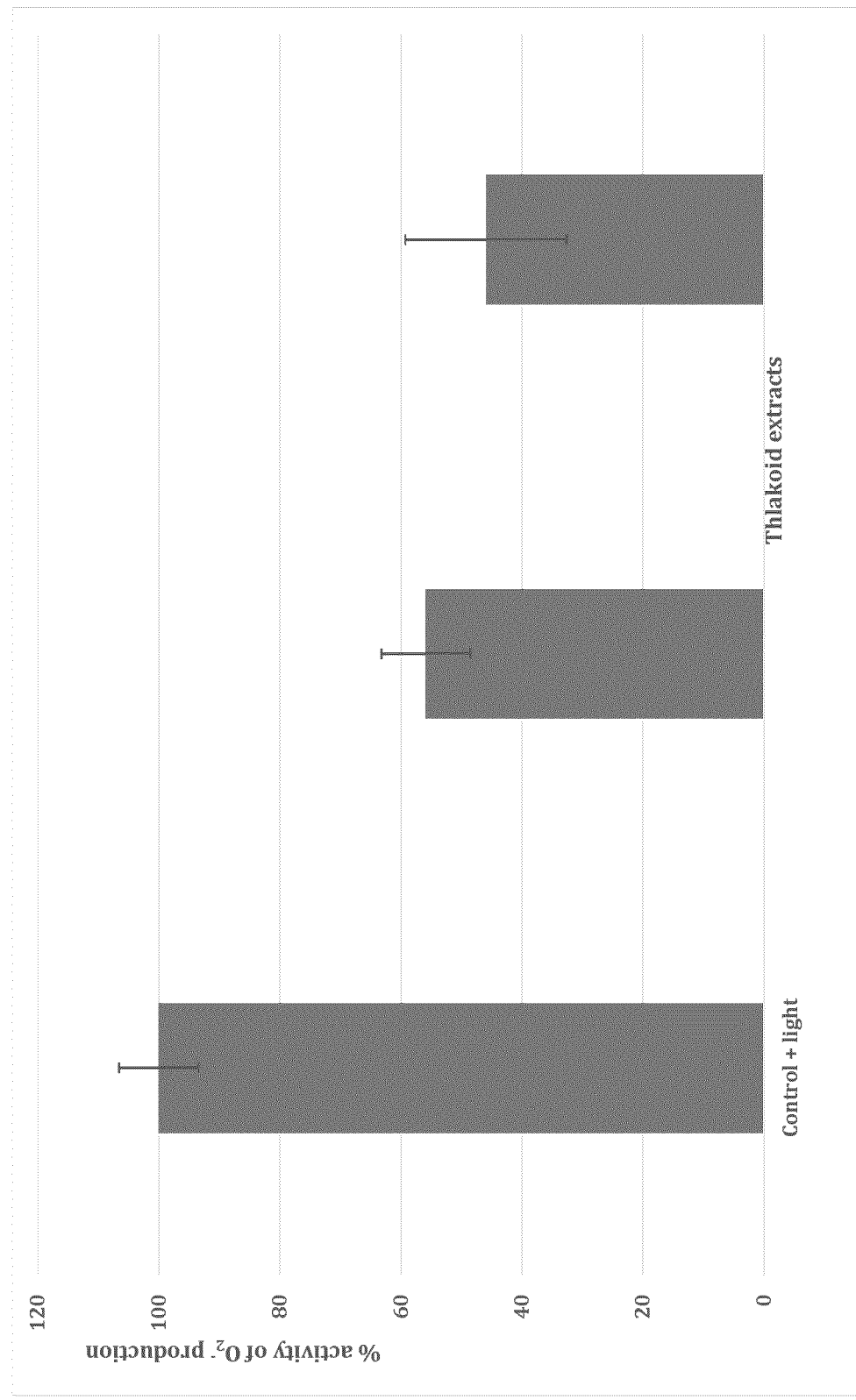
FIG. 8. Inhibition of superoxides by the functional thylakoid extract of the present invention.

Results presented in FIG. 8 show the capacity of thylakoid extracts to inhibit the production of superoxides ($O_2^-$). In both tested extracts, the remaining superoxide generation activity was 55 and 45% relative to the control. This inhibition of $O_2^-$ corresponds to 1,2535 and 1,597 mU SOD/g of proteins, respectively.

Relationship Between Anti-Inflammatory and Antioxidant Activities of Thylakoids Related to Cardiovascular Diseases.

By inhibiting iNOS and therefore decreasing deleterious NO levels, the present data demonstrate that thylakoid extracts have anti-inflammatory properties. Furthermore, data also demonstrated that thylakoid extracts can restore the reduced antioxidant defenses associated to cardiovascular diseases. Thylakoid extracts have therefore the capacity of restoring the decreased anti-oxidant buffering capacity associated with cardiovascular diseases.

Conclusions

The data presented herein indicate that the thylakoid extract (Composition A medicinal product) of the present invention is active against ulcerative colitis. Interestingly, in addition the intestinal-specific marker: fecal lactoferrin, two general inflammation biomarkers the C-reactive protein (CRP) and high sensitivity C-reactive protein (hs CRP) are also markedly decreased upon treatment (see FIGS. 4 & 5)

indicating that inflammation may be addressed more broadly than simply at the level of the inflamed bowels.

The excellent safety profile of Composition A rectal enema to date, in both the Phase 1 and Phase 2a studies conducted, the significant reduction in rectal bleeding—a cardinal symptom of ulcerative colitis—and fecal lactoferrin levels, the marked but statistically insignificant reductions in the levels of other established biomarkers of inflammation, the exploratory biomarkers of inflammation and apoptosis (leucotriene $B_4$ and M30 apoptosome), and the trends toward superiority over placebo observed in the relief of the other key symptoms of ulcerative colitis all suggest that Composition A should be active in the treatment, or in the delayed onset, of cardiovascular diseases.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

All patents, patent applications and publications mentioned in this specification are herein incorporated by reference to the same extent as if each independent patent, patent application or publication was specifically and individually indicated to be incorporated herein by reference.

REFERENCES

Bissonnette et al., 2004; PCT-233, a novel modulator of pro- and anti-inflammatory cytokine production, Clin Exp Immunol. 435: 440-447.

Maxwell K. (2000); Chlorophyl fluorescence—a practical guide. J Exp Bot. 51: 658-668.

High sensitivity C-reactive protein: Potential adjunct for global risk assessment in the Primary prevention of cardiovascular disease, Ridker, 2001; Circulation, 103, 1813-1818.

Reduced arterial elasticity in rheumatoid arthritis and the relationship to vascular disease risk factors and inflammation; Wong et al., 2003; Arthr & Rheumatism; 48; No. 1, pp 81-89.

Should C-reactive protein be added to Metabolic syndrome and to assessment of global cardiovascular risk?; Ridker et al., 204, Circulation, 109; 2818-2825.

C-reactive protein in peripheral arterial disease: Relation to severity of the disease and to future cardiovascular events, Vainas et al., 2005: J. Vasc. Surg. Doi: vol. 42, no. 2, 243-251.

Elevated C-reactive protein lee3ls are associated with post-operative events in patients undergoing lower extremity vein bypass surgery, Owens et al., 2007; J. Vasc. Surg., vol 43, no.1, 2-9.

Prognostic significance of the centers for disease control/American heart association high-sensitivity C-reactive protein cut points for cardiovascular and other outcomes in patients with stable coronary artery disease, Sabatin et al., 2007; Circulation, 1115; 1528-1536.

Inflammation and Atherosclerosis, From pathology to practice, Libby et al., J. Am. College Cardiology, 2009, vol 54, No. 23, 2129-2136, doi:10.1016.

The role and clinical significance of high-sensitivity C-reactive protein in cardiovascular disease, Seo, 2012, Korean Circulation Journal, 42, 3, 151.

C-reactive protein beyond biomarker of inflammation in metabolic syndrome, Horiuchi et al., 2001, Hypertension, 57: 672-673.

High-sensitivity C-reactive protein and coronary heart disease mortality in patient with type-2 diabetes, Soinio et al., 2006; Diabetes care, vol. 29. No. 2, 329-333.

Soluble biomarkers differentiate patients with psoriatic arthritis from those with psoriasis without arthritis.

Relationship between the hs-CRP as non-specific biomarker and Alzheimer's disease according to aging process, Song et al. 2015, Int J Med Sci.; 12(8): 613-617.

Anti-inflammatory drugs in the treatment of neurodegenerative diseases: current state. Gilgun-Sherki et al., 2006, Curr Pharm Des.; 12(27):3509-19.

Antioxidants and neuroprotection in the adult and developing central nervous system. Kaur et al. 2008 Curr Med Chem.; 15(29):3068-80.

Albert M A. Biomarkers and heart disease. J Clin Sleep Med 2011; 7(5): Supplement S9-S11.

FDA NEWS RELEASE Feb.9, 2010. FDA Approves New Indication for: Crestor.

Genest J, Ruth McPherson, Jiri Frohlich, Todd Anderson, Norm Campbell, André Carpentier, Patrick Couture, Robert Dufour, George Fodor, Gordon A. Francis, Steven Grover, Milan Gupta, Robert A. Hegele, David C. Lau, Lawrence Leiter, Gary F. Lewis, Eva Lonn, G. B. John Mancini, Dominic Ng, Glen J. Pearson, Allan Sniderman, James A. Stone, Ehud Ur. 2009 Canadian Cardiovascular Society/Canadian guidelines for the diagnosis and treatment of dyslipidemia and prevention of cardiovascular disease in the adult—2009 recommendations. Can J Cardiol 2009; 25:567-579.

Greenland Philip, Joseph S. Alpert, George A. Beller, Emelia J. Benjamin, Matthew J. Budoff, Zahi A. Fayad, Elyse Foster, Mark. A. Hlatky, John McB. Hodgson, Frederick G. Kushner, Michael S. Lauer, Leslee J. Shaw, Sidney C. Smith, Allen J. Taylor, William S. Weintraub and Nanette K. WengerGreenland P, Alpert J S, Beller G A, et al. 2010 ACCF/AHA guideline for assessment of cardiovascular risk in asymptomatic adults: a report of the American College of Cardiology Foundation/American Heart Association Task Force on Practice Guidelines. J Am Coll Cardiol 2010; 56:e50-e103.

MEMORANDUM—DEPARTMENT OF HEALTH AND HUMAN SERVICES, Public Health Service Food and Drug Administration Center for Drug Evaluation and Research DATE: 12 Nov. 2009 FROM: Division of Metabolism and Endocrinology Products (DMEP) Office of Drug Evaluation II, Center for Drug Evaluation & Research, U.S. Food & Drug Administration SUBJECT: 15 Dec. 2008, Advisory Committee meeting for rosuvastatin (Crestor™)

Myers Gary L., Robert H. M. Christenson, Mary Cushman, Christie M. Ballantyne, Gerald R. Cooper, Christine M. Pfeiffer, Scott M. Grundy, Darwin R. Labarthe, Daniel Levy, Nader Rifai, Peter W. F. Wilson. 2009. National Academy of Clinical Biochemistry Laboratory Medicine Practice Guidelines: emerging biomarkers for primary prevention of cardiovascular disease. Clin Chem 2009; 55:378-384.

Pearson T. A, George A. Mensah, R. Wayne Alexander, Jeffrey L. Anderson, Richard O. Cannon, Michael Criqui, Yazid Y. Fadl, Stephen P. Fortmann, Yuling Hong, Gary L. Myers, Nader Rifai, Sidney C. Smith, Kathryn Taubert, Russell P. Tracy and Frank Vinicor (2003). Markers of inflammation and cardiovascular disease: application to clinical and public health practice: a statement for health-care professionals from the Centers for Disease Control and Prevention and the American Heart Association. Circulation 2003; 107: 499-511.

Ridker, P. M., Cannon C. P., Morrow D., Rifai N., Rose L. M., McCabe C. H., Pfeffer M. A, and Braunwald E., 2005. C-reactive protein levels and outcomes after statin therapy. N Engl J Med 2005; 352:20-28.

The Emerging Risk Factors Collaboration* (2012). C-Reactive Protein, Fibrinogen, and Cardiovascular Disease Prediction. N Engl J Med 2012; 367:1310-1320.

Yousuf O., Mohanty B. D., Martin S. S., Joshi P. H., Blaha M. J., Nasir K., Blumenthal R. S., Budoff M. J. 2013. J. Amer. Coll. Cardio. 62(5): 397-408.

Arcaro A., Pirozzi F., Angelini A., Chimenti C., Crotti L., Giordano C., Mancardi D., Torella D., Tocchetti C. G. (2015). Novel Perspectives in Redox Biology and Pathophysiology of Failing Myocytes: Modulation of the Intramyocardial Redox Milieu for Therapeutic Interventions—A Review Article from the Working Group of Cardiac Cell Biology, Italian Society of Cardiology. Oxidative Medicine and Cellular Longevity. Volume 2016, Article ID 6353469, 13 pages http://dx.doi.org/10.1155/2016/6353469.

Asada K. (2006). Production and Scavenging of Reactive Oxygen Species in Chloroplasts and Their Functions. Plant Physiology, Vol. 141, pp. 391-396.

Beauchamp, C. and I. Fridovich, Superoxide dismutase: improved assays and an assay applicable to acrylamide gels. Anal Biochem, 1971. 44(1): p. 276-87.

Besedina A. (2016). NO-SYNTHASE ACTIVITY IN PATIENTS WITH CORONARY HEART DISEASE ASSOCIATED WITH HYPERTENSION OF DIFFERENT AGE GROUPS. J Med Biochem 35: 43-49, 2016 J Med Biochem 35: 43-49, 2016.

Chan E D, Riches D W. (2001). IFN-gamma+LPS induction of iNOS is modulated by ERK, JNK/SAPK, and p38(ma pk) in a mouse macrophage cell line Am J Physiol Cell Physiol. 2001 March; 280(3):C441-50.

Fukai T. and Ushio-Fukai M. (2011). Superoxide Dismutases: Role in Redox Signaling, Vascular Function, and Diseases. ANTIOXIDANTS & REDOX SIGNALING Volume 15, Number 6, 2011.

Jawalekar S. L., Kulkarni U. J., Surve V. T. Deshmukh Y. A. (2010). Role of Oxidants and Anti-Oxidants in Patients with Cardiovascular Diseases. Asian Journal of Medical Sciences 2(4): 181-184.

Koide N, Mu M M, Hassan F, Islam S, Tumurkhuu G, Dagvadorj J, Naiki Y, Mori I, Yoshida T, Yokochi T (2007). Lipopolysaccharide enhances interferon-gamma-induced nitric oxide (NO) production in murine vascular endothelial cells via augmentation of interferon regulatory factor-1 activation. J Endotoxin Res. 2007; 13(3): 167-75.

Kuo, W., et al., Cellular Extract Preparation for Superoxide Dismutase (SOD) Activity Assay. Bio-protocol, 2013. 3(13).

Li Q, Youn J Y, Cai H. (2015). Mechanisms and consequences of endothelial nitric oxide synthase dysfunction in hypertension. J Hypertens. 33(6):1128-36.

McNeill E. and Channon K. M. (2012). The role of tetrahydrobiopterin in inflammation and cardiovascular disease. Thromb Haemost. 108(5): 832-83.

Pall M. L. (2013). The NO/ONOO-Cycle as the Central Cause of Heart Failure. Int J Mol Sci. 14(11): 22274-22330.

van Deel E. D., Lu Z., Xu X., Zhu G., Hu X., Oury T. D., Bache R. J., Duncker D. J., and Chen Y. (2008). Extracellular SOD protects the heart against oxidative stress and hypertrophy after myocardial infarction. Free Radic Biol Med. 2008 Apr. 1; 44(7): 1305-1313.

Wu X, Beecher G. R., Holden J. M., Haytowitz D. B., Gebhardt S. E., Prior R. L. (2004). Lipophilic and Hydrophilic Antioxidant Capacities of Common Foods in the United States. J. Agric. Food Chem., 52 (12), 4026-4037.

Zhang P Y, Xu X, Li X C. (2014). Cardiovascular diseases: oxidative damage and antioxidant protection. Eur Rev Med Pharmacol Sci. 18(20):3091-3096.

Zimmerman M. C. (2011). Angiotensin II and Angiotensin-1-7 Redox Signaling in the Central Nervous System. Curr Opin Pharmacol 11(2): 138-143.

Tian W, Jiang X, Tamosiuniene R, Sung Y K, Qian J, Dhillon G, Gera L, Farkas L, Rabinovitch M, Zamanian R T, Inayathullah M, Fridlib M, Rajadas J, Peters-Golden M, Voelkel N F, Nicolls M R. (2013). Blocking macrophage leukotriene b4 prevents endothelial injury and reverses pulmonary hypertension. Sci Transl Med. 28; 5(200): 200ra117.

The invention claimed is:

1. A method for treating cardiovascular diseases (CVD) in a subject in need thereof, comprising administering to said subject an effective amount of a thylakoid extract comprising purified functional photosynthetic pigments in their thylakoid membrane environment, in admixture with a physiologically acceptable carrier, wherein said amount of extract is about 0.00005 to about 500 mg per Kg of the subject's body weight.

2. The method of claim 1, wherein said extract is stabilized in a medium comprising less than 10% of electron donor.

3. The method of claim 2, wherein said medium comprises less than 10% of water.

4. The method of claim 1, wherein said extract is for oral administration.

5. The method of claim 1, wherein said extract is formulated for parenteral administration.

6. The method of claim 1, wherein said extract is formulated intra-cardiac administration immediately after a heart attack.

7. The method of claim 1, wherein said extract is formulated intra-cardiac administration up to 24 hours after a heart attack.

8. The method of claim 1, wherein said CVD is selected from: angina, stroke, myocardial/cerebral infraction, atherosclerosis, bypass surgery, ischemia, hypertensive heart disease, rheumatic heart disease, cardiomyopathy, heart arrhythmia, congenital heart disease, valvular heart disease, carditis, aortic aneurysms, peripheral artery disease, and venous thrombosis.

9. The method of claim 8, wherein said CVD is angina, stroke, myocardial infraction, ischemia, venous thrombosis and atherosclerosis.

10. The method of claim 1, wherein said amount of extract is about 0.05 to about 10 mg per Kg of subject's body weight.

11. The method of claim 1, wherein the extract is in a dosage selected from: about 125 mg, about 200 mg, about 250 mg, about 500 and 1000 mg per day.

* * * * *